US010899824B2

(12) United States Patent
Burioni et al.

(10) Patent No.: US 10,899,824 B2
(45) Date of Patent: Jan. 26, 2021

(54) ANTI-HSV SYNERGISTIC ACTIVITY OF ANTIBODIES AND ANTIVIRAL AGENTS

(71) Applicant: Polichem S.A., Luxembourg (LU)

(72) Inventors: Roberto Burioni, Milan (IT); Massimo Clementi, Milan (IT)

(73) Assignee: Polichem S.A., Luxembourg (LU)

( * ) Notice: Subject to any disclaimer, the term of this patent is extended or adjusted under 35 U.S.C. 154(b) by 0 days.

(21) Appl. No.: 16/319,541

(22) PCT Filed: Jul. 26, 2017

(86) PCT No.: PCT/EP2017/068912
§ 371 (c)(1),
(2) Date: Jan. 22, 2019

(87) PCT Pub. No.: WO2018/019897
PCT Pub. Date: Feb. 1, 2018

(65) Prior Publication Data
US 2019/0185546 A1 Jun. 20, 2019

(30) Foreign Application Priority Data
Jul. 26, 2016 (EP) ..................................... 16181160

(51) Int. Cl.
| | | |
|---|---|---|
| *C07K 16/08* | (2006.01) | |
| *A61K 31/522* | (2006.01) | |
| *A61K 31/662* | (2006.01) | |
| *A61K 39/42* | (2006.01) | |
| *A61K 45/06* | (2006.01) | |
| *A61P 31/22* | (2006.01) | |
| *A61P 27/00* | (2006.01) | |
| *A61K 39/00* | (2006.01) | |

(52) U.S. Cl.
CPC .......... *C07K 16/087* (2013.01); *A61K 31/522* (2013.01); *A61K 31/662* (2013.01); *A61K 39/42* (2013.01); *A61K 45/06* (2013.01); *A61P 27/00* (2018.01); *A61P 31/22* (2018.01); *A61K 2039/505* (2013.01); *C07K 2317/21* (2013.01); *C07K 2317/55* (2013.01); *C07K 2317/622* (2013.01); *C07K 2317/76* (2013.01); *C07K 2317/92* (2013.01); *C12N 2710/16611* (2013.01)

(58) Field of Classification Search
CPC ............ C07K 16/087; C07K 2317/622; C07K 2317/92; C07K 2317/76; C07K 2317/55; C07K 2317/21; A61K 39/42; A61K 45/06; A61K 31/522; A61K 31/662; A61K 2039/505; A61P 31/22; A61P 27/00; C12N 2710/16611
See application file for complete search history.

(56) References Cited

U.S. PATENT DOCUMENTS

2010/0172906 A1  7/2010  Lai et al.

FOREIGN PATENT DOCUMENTS

| EP | 2 308 895 | 4/2011 |
| EP | 3 050 897 | 8/2016 |
| WO | WO 2010/129033 | 11/2010 |
| WO | WO 2011/104687 | 9/2011 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14.*
Kussie PH, Parhami-Seren B, Wysocki LJ, Margolies MN. A single engineered amino acid substitution changes antibody fine specificity. J Immunol. Jan. 1, 1994;152(1):146-52.*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714.*
Sela-Culang I, Kunik V, Ofran Y. The structural basis of antibody-antigen recognition. Front Immunol. Oct. 8, 2013;4:302.*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.*
Murga JD, Franti M, Pevear DC, Maddon PJ, Olson WC. Potent antiviral synergy between monoclonal antibody and small-molecule CCR5 inhibitors of human immunodeficiency virus type 1. Antimicrob Agents Chemother. Oct. 2006;50(10):3289-96.*
Aoki et al., "Single-Day, Patient-Initiated Famciclovir Therapy for Recurrent Genital Herpes: A Randomized, Double-Blind, Placebo-Controlled Trial," *Clinical Infectious Diseases* 42:8-13 (2006) Published online Nov. 23, 2005.
Berstein et al., "Epidemiology, Clinical Presentation, and Antibody Response to Primary Infection With Herpes Simplex Virus Type 1 and Type 2 in Young Women," *Clinical Infectious Diseases* 56(3):344-51 (2013) Published online Oct. 19, 2012.

(Continued)

*Primary Examiner* — Rachel B Gill
(74) *Attorney, Agent, or Firm* — Klarquist Sparkman, LLP

(57) ABSTRACT

The present invention relates to a combination comprising HSV-1 and HSV-2 binding monoclonal antibodies or fragments thereof and antiviral agents, the pharmaceutical formulations comprising said combination, optionally together with an excipient pharmaceutically acceptable and its use in the prophylaxis and/or treatment of herpes virus infections, including genital herpes, HSV gingivostomatitis and recurrent herpes labialis, herpes simplex encephalitis (HSE), neonatal HSV, HSV disease in the immunocompromised host and HSV keratitis keratoconjunctivitis.

15 Claims, 5 Drawing Sheets
Specification includes a Sequence Listing.

(56) References Cited

OTHER PUBLICATIONS

Bodsworth et al., "Valaciclovir versus aciclovir in patient initiated treatment of recurrent genital herpes: a randomised, double blind clinical trial," *Genitourin Med* 73: 110-116 (Apr. 1, 1997).
Bradley et al., "Seroprevalence of Herpes Simplex Virus Types 1 and 2—United States, 1999-2010," *The Journal of Infectious Diseases* 209:325-333 (2014) Published online Oct. 16, 2013.
Brown et al., "Neonatal Herpes Simplex Virus Infection in Relation to Asymptomatic Maternal Infection at the Time of Labor," *The New England Journal of Medicine* 324(18) (1991).
Brown et al., "Effect of Serologic Status and Cesarean Delivery on Transmission Rates of Herpes Simplex Virus From Mother to Infant," *Journal of the American Medical Association* 289(2) (Jan. 8, 2003).
Chosidow et al., "Famciclovir vs. aciclovir in immunocompetent patients with recurrent genital herpes infections: a parallel-groups, randomized, double-blind clinical trial," *British Journal of Dermatology* 144:181-824 (2001).
Chou, "Theoretical Basis, Experimental Design, and Computerized Simulation of Synergism and Antagonism in Drug Combination Studies," *Pharmacol Rev* 58(3):621-681 (2006).
Corey et al., "Once-Daily Valacyclovir to Reduce the Risk of Transmission of Genital Herpes," *The New England Journal of Medicine* 350(1):11-20 (Jan. 1, 2004).
Diaz-Mitoma et al., "Oral Famciclovir for the Suppression of Recurrent Genital Herpes," *Journal of the American Medical Association* 280(10):887-892 (Sep. 9, 1998).
Fife et al., "Recurrence and Resistance Patterns of Herpes Simplex Virus following Cessation of ≥6 Years of Chronic Suppression with Acyclovir," *The Journal of Infectious Diseases* 169:1338-1341 (1994).
Fife et al., "Valaciclovir Versus Acyclovir in the Treatment of First-Episode Genital Herpes Infection," *Sexually Transmitted Diseases* 24:481-486 (Sep. 1997).
Goldberg et al., "Long-term Suppression of Recurrent Genital Herpes With Acyclovir," *Arch Dermatol* 129:582-587 (May 1993).
Krawczyk et al., "Overcoming drug-resistant herpes simplex virus (HSV) infection by a humanized antibody," *Proc Natl Acad Sci USA* 110(17): 6760-6765 (Apr. 23, 2013).
Leone et al., "Valacyclovir for Episodic Treatment of Genital Herpes: A Shorter 3-Day Treatment Course Compared with 5-Day Treatment," *Clinical Infectious Diseases* 34:958-962 (2002) Published online Feb. 20, 2002.
Mertz et al., "Oral Famciclovir for Suppression of Recurrent Genital Herpes Simplex Virus Infection in Women," *Arch Intern Med* 157:343-349 (Feb. 10, 1997).
Pinninti et al., "Neonatal Herpes Disease following Maternal Antenatal Antiviral Suppressive Therapy: A Multicenter Case Series," *The Journal of Pediatrics* 161(1):134-138 (Jul. 2012).
Reitano et al., "Valacyclovir for the Suppression of Recurrent Genital Herpes Simplex Virus Infection: A Large-Scale Dose Range—Finding Study," *Journal of Infectious Diseases* 178:603-610 (1998).
Roberts et al., "Increasing Proportion of Herpes Simplex Virus Type 1 as a Cause of Genital Herpes Infection in College Students," *Sexually Transmitted Diseases* 30:797-800 (Oct. 2003).
Romanowski et al., "Patients' Preference of Valacyclovir Once-Daily Suppressive Therapy Versus Twice-Daily Episodic Therapy for Recurrent Genital Herpes," *Sexually Transmitted Diseases* 30(3):226-231 (2003).
Ryder et al., "Increasing role of herpes simplex virus type 1 in first episode anogenital herpes in heterosexual women and younger men who have sex with men, 1992-2006," *Sexually Transmitted Infections* 85:416-419 (Mar. 9, 2009).
Solforosi et al., "A phage display vector optimized for the generation of human antibody combinatorial libraries and the molecular cloning of monoclonal antibody fragments," *New Microbiologica* 35(3):289-294 (2012).
Wald et al., "Two-Day Regimen of Acyclovir for Treatment of Recurrent Genital Herpes Simplex Virus Type 2 Infection," *Clinical Infectious Diseases* 34:944-948 (Feb. 20, 2002).
Workowski et al., "Sexually Transmitted Diseases Treatment Guidelines, 2015," *Centers for Disease Control and Prevention Morbidity and Mortality Weekly Report* 64(3) (Jun. 5, 2015).

\* cited by examiner

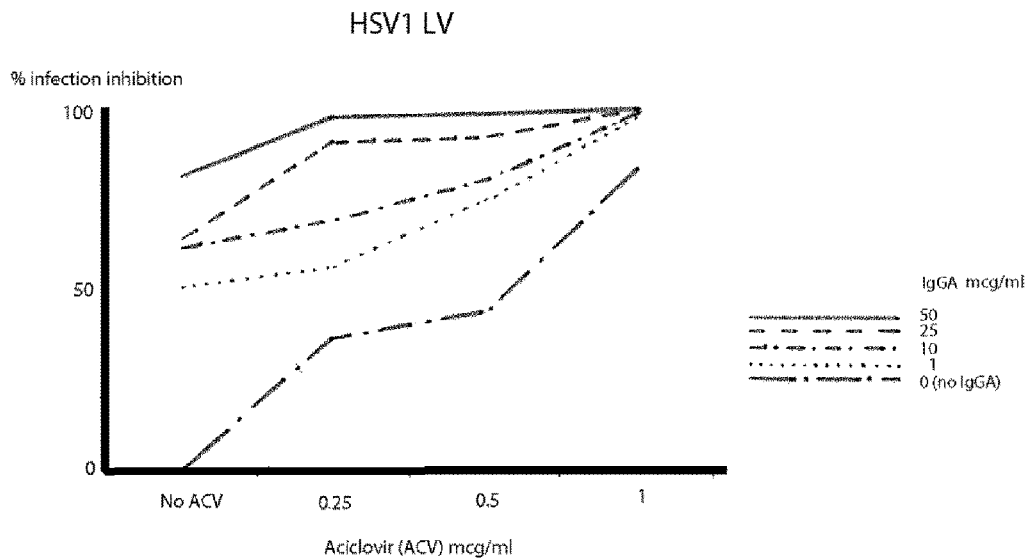
Figure 1. The graph shows how IgGA can significantly increase the inhibitory effects of ACV at the different ACV concentrations tested.
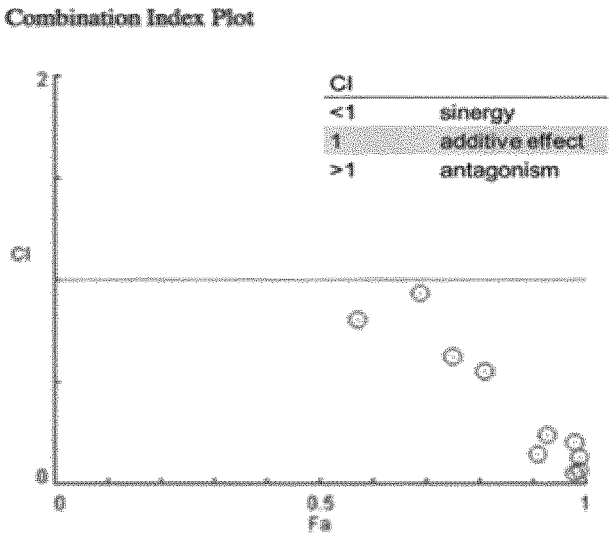
Figure 2. All the combinations of IgGA and ACV (empty circles) are below the CI value =1. This means that all the combinations of drugs have synergistic activity.

| CI Data for Non-Constant Combo: percin (IgGA+ACV) | | | |
|---|---|---|---|
| Dose IgGA | Dose ACV | Effect | CI |
| 1.0 | 0.25 | 0.57 | 0.80536 |
| 1.0 | 0.5 | 0.75 | 0.62354 |
| 1.0 | 1.0 | 0.98 | 0.20531 |
| 10.0 | 0.25 | 0.69 | 0.93915 |
| 10.0 | 0.5 | 0.81 | 0.55378 |
| 10.0 | 1.0 | 0.99 | 0.13155 |
| 25.0 | 0.25 | 0.91 | 0.15084 |
| 25.0 | 0.5 | 0.93 | 0.23928 |
| 25.0 | 1.0 | 0.99 | 0.13156 |
| 50.0 | 0.25 | 0.98 | 0.05148 |
| 50.0 | 0.5 | 0.99 | 0.06579 |
| 50.0 | 1.0 | 0.99 | 0.13157 |

Figure 3. Different CI values associated to different drug combinations. Very strong synergism and strong synergism are highlighted by boxes.

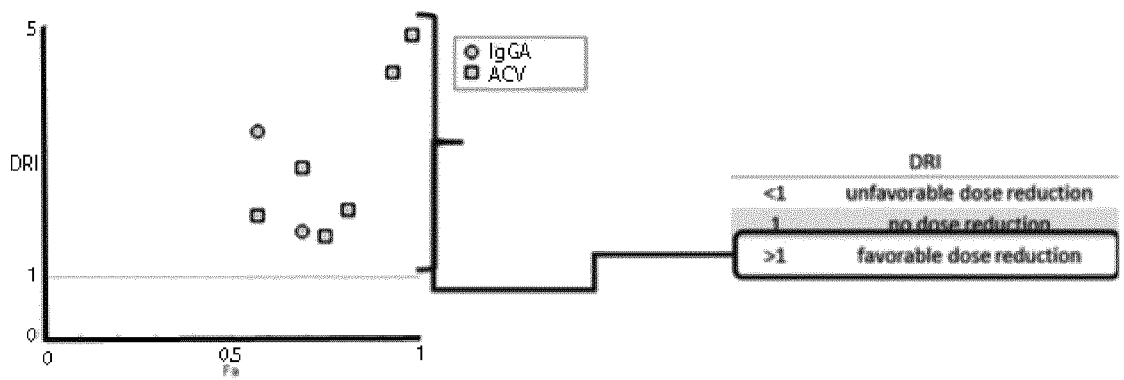

Figure 4. All the IgGA/ACV combinations result in favourable dose reduction (all the values for both IgGA and ACV lie above the Dose Reduction Index (DRI) threshold).

CI Data for Non-Constant Combo: FOS1 (IgGA+FOS)

| Dose IgGA | Dose FOS | Effect | CI |
|---|---|---|---|
| 1.0 | 0.5 | 0.09 | 0.44992 |
| 1.0 | 25.0 | 0.23 | 0.37644 |
| 1.0 | 100.0 | 0.76 | 0.34583 |
| 10.0 | 0.5 | 0.16 | 0.87283 |
| 10.0 | 25.0 | 0.32 | 0.35851 |
| 10.0 | 100.0 | 0.78 | 0.32408 |
| 25.0 | 0.5 | 0.19 | 1.29861 |
| 25.0 | 25.0 | 0.41 | 0.29955 |
| 25.0 | 100.0 | 0.96 | 0.10468 |
| 50.0 | 0.5 | 0.32 | 0.46699 |
| 50.0 | 25.0 | 0.56 | 0.18745 |
| 50.0 | 100.0 | 0.99 | 0.04537 |

Fig. 5. Different CI values associated to different IgGA and FOS combinations in HSV-1.

CI Data for Non-Constant Combo: FOS2 (IgGA+FOS)

| Dose IgGA | Dose FOS | Effect | CI |
|---|---|---|---|
| 1.0 | 5.0 | 0.25 | 0.66752 |
| 1.0 | 10.0 | 0.25 | 0.81607 |
| 1.0 | 25.0 | 0.32 | 0.86835 |
| 20.0 | 5.0 | 0.42 | 1.89039 |
| 20.0 | 10.0 | 0.4 | 2.37008 |
| 20.0 | 25.0 | 0.55 | 0.94709 |
| 50.0 | 5.0 | 0.53 | 1.72052 |
| 50.0 | 10.0 | 0.54 | 1.65819 |
| 50.0 | 25.0 | 0.7 | 0.61048 |
| 100.0 | 5.0 | 0.77 | 0.32759 |
| 100.0 | 10.0 | 0.84 | 0.18070 |
| 100.0 | 25.0 | 0.84 | 0.30154 |

Fig. 6. Different CI values associated to different IgGA and FOS combinations in HSV-2.

CI Data for Non-Constant Combo: PCV1 (IgGA+PCV)

| Dose IgGA | Dose PCV | Effect | CI |
|---|---|---|---|
| 1.0 | 0.5 | 0.61 | 0.38835 |
| 1.0 | 0.75 | 0.63 | 0.53929 |
| 1.0 | 1.5 | 0.74 | 0.93696 |
| 10.0 | 0.5 | 0.7 | 0.48049 |
| 10.0 | 0.75 | 0.7 | 0.63952 |
| 10.0 | 1.5 | 0.78 | 0.94778 |
| 25.0 | 0.5 | 0.72 | 0.62007 |
| 25.0 | 0.75 | 0.78 | 0.57043 |
| 25.0 | 1.5 | 0.94 | 0.73101 |
| 50.0 | 0.5 | 0.82 | 0.40608 |
| 50.0 | 0.75 | 0.91 | 0.39949 |
| 50.0 | 1.5 | 0.9999 | 0.29323 |

Figure 7. Different CI values associated to different IgGA and PCV combinations in HSV-1.

CI Data for Non-Constant Combo: PCV2 (IgGA+PCV)

| Dose IgGA | Dose PCV | Effect | CI |
|---|---|---|---|
| 1.0 | 1.5 | 0.29 | 0.75926 |
| 1.0 | 2.5 | 0.29 | 1.14652 |
| 1.0 | 7.0 | 0.81 | 0.74742 |
| 20.0 | 1.5 | 0.59 | 1.01976 |
| 20.0 | 2.5 | 0.66 | 0.90923 |
| 20.0 | 7.0 | 0.94 | 0.39477 |
| 50.0 | 1.5 | 0.85 | 0.46046 |
| 50.0 | 2.5 | 0.85 | 0.55050 |
| 50.0 | 7.0 | 0.98 | 0.21204 |
| 100.0 | 1.5 | 0.93 | 0.30682 |
| 100.0 | 2.5 | 0.98 | 0.11109 |
| 100.0 | 7.0 | 0.9999 | 0.01003 |

Figure 8. Different CI values associated to different IgGA and PCV combinations in HSV-2.

CI Data for Non-Constant Combo: GCV1 (IgGA+GCV)

| Dose IgGA | Dose GCV | Effect | CI |
|---|---|---|---|
| 1.0 | 0.05 | 0.35 | 0.45706 |
| 1.0 | 0.25 | 0.62 | 0.75355 |
| 1.0 | 0.75 | 0.9999 | 0.00468 |
| 10.0 | 0.05 | 0.5 | 0.68740 |
| 10.0 | 0.25 | 0.66 | 0.80463 |
| 10.0 | 0.75 | 0.9999 | 0.00468 |
| 25.0 | 0.05 | 0.51 | 1.32378 |
| 25.0 | 0.25 | 0.72 | 0.77484 |
| 25.0 | 0.75 | 0.9999 | 0.00468 |
| 50.0 | 0.05 | 0.66 | 0.91254 |
| 50.0 | 0.25 | 0.84 | 0.46688 |
| 50.0 | 0.75 | 0.9999 | 0.00468 |

Figure 9. Different CI values associated to different IgGA and GCV combinations in HSV-1.

CI Data for Non-Constant Combo: GCV2 (IgGA+GCV)

| Dose IgGA | Dose GCV | Effect | CI |
|---|---|---|---|
| 1.0 | 0.01 | 0.28 | 0.73892 |
| 1.0 | 0.1 | 0.42 | 0.85294 |
| 1.0 | 0.5 | 0.86 | 0.51699 |
| 20.0 | 0.01 | 0.6 | 1.45631 |
| 20.0 | 0.1 | 0.64 | 1.37122 |
| 20.0 | 0.5 | 0.89 | 0.49659 |
| 50.0 | 0.01 | 0.72 | 1.50656 |
| 50.0 | 0.1 | 0.77 | 1.13893 |
| 50.0 | 0.5 | 0.93 | 0.36935 |
| 100.0 | 0.01 | 0.88 | 0.55259 |
| 100.0 | 0.1 | 0.92 | 0.32234 |
| 100.0 | 0.5 | 0.97 | 0.17433 |

Figure 10. Different CI values associated to different IgGA and GCV combinations in HSV-2.

ANTI-HSV SYNERGISTIC ACTIVITY OF ANTIBODIES AND ANTIVIRAL AGENTS

CROSS REFERENCE TO RELATED APPLICATIONS

This is the U.S. National Stage of International Application No. PCT/EP2017/068912, filed Jul. 26, 2017, which was published in English under PCT Article 21(2), which in turn claims the benefit of European Application No. 16181160.9, filed Jul. 26, 2016. Both applications are incorporated herein by reference in their entireties.

BACKGROUND OF THE INVENTION

Herpes simplex viruses (HSV) infection-related diseases are a global health problem due to the high infection rates of the general population. Clinical manifestations include small, painful, vesicles affecting the skin, mouth, lips, eyes, or genitalia, and systemic symptoms such as fever and malaise. According to the affected organ, the herpes virus infections are classified in genital herpes, HSV gingivostomatitis and recurrent herpes labialis, herpes simplex encephalitis (HSE), neonatal HSV, HSV disease in the immunocompromised host and HSV keratitis or keratoconjunctivitis.

HSV persists in sensory and autonomic neural ganglions for the life of the host and periodically reactivates. Clinical recurrences are triggered by several stimuli, such as stress, menstrual periods, fever or illness, sun exposure or sunburn.

The clinical course of HSV infection is strongly influenced by the immune status of the host with severe and life-threatening infections occurring in newborns and immune-compromised patients.

Genital herpes is a chronic, life-long viral infection. Two types of HSV can cause genital herpes: HSV-1 and HSV-2. Most cases of recurrent genital herpes are caused by HSV-2, and approximately 50 million persons in the United States are infected with this type of genital herpes (1). However, an increasing proportion of anogenital herpetic infections have been attributed to HSV-1 infection, which is especially prominent among young women and men who have sex with men (MSM) (2-4). As most persons infected with HSV-2 do not have the condition diagnosed, most genital herpes infections are transmitted by persons unaware of the infection or asymptomatic when the transmission occurs. Management of genital HSV should address the chronic nature of the disease rather than focusing solely on treatment of acute episodes of genital lesions (5).

Antiviral chemotherapy offers clinical benefits to most symptomatic patients and is the mainstay of management. Counseling regarding the natural history of genital herpes, sexual and perinatal transmission, and methods to reduce transmission is integral to clinical management.

Systemic antiviral drugs can partially control the signs and symptoms of genital herpes when used to treat first clinical and recurrent episodes or when used as daily suppressive therapy. However, these drugs neither eradicate latent virus nor affect the risk, frequency, or severity of recurrences after the drug is discontinued. Randomized trials have indicated that three antiviral medications provide clinical benefit for genital herpes: acyclovir, valacyclovir, and famciclovir (6-14). Valacyclovir is the valine ester of acyclovir and has enhanced absorption after oral administration. Famciclovir also has high oral bioavailability. These drugs are not curative, but may reduce the pain of a herpes outbreak and shorten the period of viral shedding. Topical therapy with antiviral drugs offers minimal clinical benefit and is discouraged. Almost all persons with symptomatic first-episode genital HSV-2 infection subsequently experience recurrent episodes of genital lesions; recurrences are less frequent after initial genital HSV-1 infection. Intermittent asymptomatic shedding occurs in persons with genital HSV-2 infection, even in those with longstanding or clinically silent infection. Antiviral therapy for recurrent genital herpes can be administered either as suppressive therapy to reduce the frequency of recurrences or episodically to ameliorate or shorten the duration of lesions. Some patients, including those with mild or infrequent recurrent outbreaks, benefit from episodic antiviral therapy. Many persons prefer suppressive therapy, which has the additional advantage of decreasing the risk for genital HSV-2 transmission to susceptible partners (15, 16). Suppressive therapy reduces the frequency of genital herpes recurrences by 70%-80% in patients who have frequent recurrences (12-15), many persons receiving such therapy report having experienced no symptomatic outbreaks. Efficacy has been documented among patients receiving daily therapy with acyclovir for as long as 6 years and with valacyclovir or famciclovir for 1 year. Quality of life is improved in many patients with frequent recurrences who receive suppressive therapy rather than episodic treatment (17-18)

Treatment with valacyclovir 500 mg daily decreases the rate of HSV-2 transmission in discordant, heterosexual couples in which the source partner has a history of genital HSV-2 infection.

Intravenous (IV) acyclovir therapy should be provided for patients who have severe HSV disease or complications that necessitate hospitalization (e.g., disseminated infection, pneumonitis, or hepatitis) or CNS complications (e.g., meningoencephalitis).

If lesions persist or recur in a patient receiving antiviral treatment, HSV resistance should be suspected and a viral isolate obtained for sensitivity testing. Cross-resistance is known among acyclovir, valacyclovir and famciclovir. In case of resistance to acyclovir, foscarnet may be an alternative. In fact, this drug has a different mechanism of action (viral DNA and RNA polymerase inhibitor) and less chance of cross-resistance. Clinical management of antiviral resistance remains challenging among persons with HIV infection, necessitating other preventative approaches.

Genital herpes in pregnancy: the risk for transmission to the neonate from an infected mother is high (30%-50%) among women who acquire genital herpes close to the time of delivery and low (<1%) among women with prenatal histories of recurrent herpes or who acquire genital HSV during the first half of pregnancy (19-20). Newborn infants exposed to HSV during birth, as documented by maternal virologic testing of maternal lesions at delivery or presumed by observation of maternal lesions may develop a disease limited to the skin and mucous membranes, or a high-risk disseminated disease with involvement also of the central nervous system.

Prevention of neonatal herpes depends both on preventing acquisition of genital HSV infection during late pregnancy and avoiding exposure of the neonate to herpetic lesions and viral shedding during delivery.

Although cesarean delivery does not completely eliminate the risk for HSV transmission to the neonate, women with recurrent genital herpetic lesions at the onset of labor should deliver by cesarean delivery to reduce the risk for neonatal HSV infection.

Acyclovir can be administered orally to pregnant women with first-episode genital herpes or recurrent herpes and should be administered IV to pregnant women with severe HSV infection. Suppressive acyclovir treatment late in pregnancy reduces the frequency of cesarean delivery among women who have recurrent genital herpes by diminishing the frequency of recurrences at term. However, such treatment may not protect against transmission to neonates in all cases (21).

In conclusion, antiviral therapy is available to treat HSV infection, but this is active only in 80% of patients, it induces resistances and cross-resistance is reported among the only three antiviral products recommended by the STD treatment guidelines for HSV, namely acyclovir, valacyclovir and famciclovir, and the fourth product, foscarnet as a second line. Although other antiviral agents, such as penciclovir and ganciclovir, became commercially available in recent times, those new agents do not seem to fully meet the unmet medical need. Furthermore, those products have a level of toxicity for several organs, including renal toxicity, liver toxicity, and neurotoxicity, with dose- and time-related severity. This may be even more problematic considering the need to treat the patients lifelong to achieve a suppressive therapy. Therefore, new approaches are needed in terms both of efficacy and safety.

A way to improve the anti HSV therapy, in particular in case of resistance to antiviral drugs, has been proposed by Krawczyk et al. (22), who constructed a murine humanized anti HSV antibody, able to neutralize HSV1 viruses, either laboratory strains, or clinical isolates, independently on their susceptibility or resistance to acyclovir, cidofovir or foscarnet. That antibody may improve the therapy of those patients, but it leaves two unsolved problems: first, it is less active on HSV2 viruses, both laboratory strains, and clinical isolates, and requires higher concentrations to neutralize HSV2 than HSV1. Furthermore, being a murine humanized antibody, it is endowed with an intrinsic immunogenicity in humans, which does not predict its possible long-term use.

It is therefore increasingly felt the need for novel strategies and options in fighting herpes infections.

BRIEF DESCRIPTION OF THE FIGURES

FIG. 1 is a graph showing how IgGA significantly increase the inhibitory effects of different concentrations of ACV FIG. 2 shows the sinergistic activity of the combinations IgGA and ACV.

FIG. 3 is a table showing different CI values associated to different drug combinations.

FIG. 4 is a graph showing the IgGA/ACV combinations that results in a favorable dose reduction.

FIG. 5 shows the CI values associated to different drug combination of IgGA and Foscarnet in HSV-1.

FIG. 6 shows the CI values associated to different drug combination of IgGA and Foscarnet in HSV-2.

FIG. 7 shows the CI values associated to different drug combination of IgGA and Penciclovir in HSV-1.

FIG. 8 shows the CI values associated to different drug combination of IgGA and Penciclovir in HSV-2.

FIG. 9 shows the CI values associated to different drug combination of IgGA and Ganciclovir in HSV-1.

FIG. 10 shows the CI values associated to different drug combination of IgGA and Ganciclovir in HSV-2.

DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "simultaneous, separate or sequential administration" herein refers to administration of the first and second compound at the same time or in such a manner that the two compound act in the patient's body at the same time or administration of one compound after the other compound in such a manner to provide a therapeutic effect. In some embodiments the compounds are taken with a meal. In other embodiments, the compounds are taken after a meal, such as 30 minutes or 60 minutes after a meal. In some embodiments, one compound is administered to a patient for a time period followed by administration of the other compound.

The term "HSV" as used herein refers to Herpes Simplex Virus. There are two types of HSV, namely HSV-1 and HSV-2 which show similar characteristics.

The monoclonal antibodies and the fragments thereof of the present invention bind to HSV-1 and/or HSV-2 and can inhibit HSV infections.

The term "fragment" of antibodies which bind to HSV-1 and/or to HAS-2 refers to Fab, or single chain antibody fragments "scFv fragment" which have smaller size with respect to the corresponding antibody.

The term "Fab fragment" (fragment antigen-binding) and "Fab2 fragment" refers to immunoglobulin fragments consisting of a light chain linked to the Fc fragment of the adjacent heavy chain, and such fragments are monovalent antibodies. When the Fab portions are in pairs, the fragment is called Fab2.

The term "scFv fragment" (single chain variable fragment) refers to immunoglobulin fragments only capable of binding with the antigen concerned. ScFv fragments can also be synthesized into dimers (diabodies), trimers (triabodies) and tetramers (tetrabodies) using peptide linkers.

For the purposes of the present invention, each antibody region has a corresponding SEQ ID NO., as follows:

SEQ ID NO.1 corresponds to the amino acidic sequence of the heavy chain (VH) variable region of the VH1 antibody, also identified as Fab Ex2;

SEQ ID NO.2 corresponds to the amino acidic sequence of the light chain (VL) variable region of the VH1 antibody, also identified as Fab Ex2;

SEQ ID NO.3 corresponds to the amino acidic sequence of the complementary determining regions of the VH1 antibody, also identified as Fab Ex2;

SEQ ID NO.4 corresponds to the amino acidic sequence of the heavy chain (VH) variable region of the VH3 antibody, also identified as Fab Ex2B and of the VH51, also identified as Fab Ex2I SEQ ID NO.5 corresponds to the amino acidic sequence of the light chain (VL) variable region of the VH3 antibody, also identified as Fab Ex2B;

SEQ ID NO.6 corresponds to the amino acidic sequence of the complementary determining regions of the VH3 antibody, also identified as Fab Ex2B and of the VH51, also identified as Fab Ex2I;

SEQ ID NO.7 corresponds to the amino acidic sequence of the heavy chain (VH) variable region of the VH5 antibody, also identified as Fab Ex2C;

SEQ ID NO.8 corresponds to the amino acidic sequence of the light chain (VL) variable region of the VH5 antibody, also identified as Fab Ex2C;

SEQ ID NO.9 corresponds to the amino acidic sequence of the complementary determining regions of the VH5 antibody, also identified as Fab Ex2C;

SEQ ID NO.10 corresponds to the amino acidic sequence of the heavy chain (VH) variable region of the VH47 antibody, also identified as Fab Ex2H;

SEQ ID NO.11 corresponds to the amino acidic sequence of the light chain (VL) variable region of the VH47 antibody, also identified as Fab Ex2H;

SEQ ID NO.12 corresponds to the amino acidic sequence of the complementary determining regions of the VH47 antibody, also identified as Fab Ex2H;

SEQ ID NO.13 corresponds to the amino acidic sequence of the light chain (VL) variable region of the VH51 antibody, also identified as Fab Ex2I.

The order in which the heavy and light chains are present in each single chain antibody may be inverted, thus a single chain antibody may be formed by a heavy chain-light chain or by a light chain-heavy chain, and the activity cannot be envisaged a priori on the basis of the chain succession.

DESCRIPTION OF THE INVENTION

It has been now surprisingly demonstrated by the inventors that a combination comprising a fully human monoclonal antibody, capable to bind and neutralize both HSV1 and HSV2 at very low concentrations, and an antiviral agents is particularly effective in the treatment of genital herpes infections.

In particular, the results of the experiments disclosed in the present invention show that the combined administration of a particular concentration of a human monoclonal antibody and of an antiviral agent is synergic, in the sense that the effect of the combination is superior to the sum of the effects of the two active principles taken alone.

A fully human mAb is certainly preferred to animal derived mAb giving the very low risk that administered human mAb could be recognized as non-self molecule leading to side effects compared to animal derived mAbs. Furthermore, an antibody produced by a subject infected by

| SEQ ID NO: | Amino acid sequence |
|---|---|
| 1 | LESGGGVVQPGRSLRLSCAASGFTFTTFAMHWVRQAPGKGLEWLAFIS YDGSNKYYADSVKGRFTISRDNSKNTLYLQMNSLRAEDTSIYYCAREVW NYADYWGQGALVTVSS |
| 2 | ELTQSPGTLSSSPGHRATLSCKASAPLGSNHMAWYQQKPGQAPRLLIY GASTRATGVPARFTGSGSGTDFTLTISSLQPEDFATYYCQQANSFPRTF GQGTKVEIK |
| 3 | EVWNYADY |
| 4 | LEQSGAEVKKPGASVRVSCQASGYTFTNYYIHWVRQAPGQGLEWMGII NPTGGSTRIAQKFQGRVTMTSDTSTSTIFMEVSSLRSEDTAIYYCARDEY KSHHYGMDVWGQGTTVTVSS |
| 5 | ELTQSPGTLSLSPGERATLSCRANESVSRSYLAWYQQRPGQAPRLLIYG ASTRATGIPARFSGSGSGTDFTLTISRLEPEDFAVYYCQHFGSSTGLTFG GGTKVEIR |
| 6 | DEYKSHHYGMDV |
| 7 | LESGGGLVQPGGSLRLSCAASGLPFNYYAMNWVRQAPGKGLEWVSGIS ANGLNTYYAESVKGRFTISRENSQNTLYLQMNSLGAEDTAVYYCAKVLV AATHYYYNGMDVWGQGTTVTVSS |
| 8 | ELTQSPVTLSLSPGERATLSCGASQSVSSSNLAWYQQKPGLAPRLLIYD ASSRATGIPDRFSGSGSGTDFTLTISRLEPEDFAVYYCQQYGSSLITFGQ GTRLEIK |
| 9 | VLVAATHYYYNGMDV |
| 10 | LEESGAEVKKPGASVRVSCKASGYTFTGYFIHWVRQAPGQGLEWMGWI NPKSGGTNYAPKFQGRVTMTRDTSISTAYMQLSSVRSDDTAVYYCARE EIPLYYDSGYGMDVWGPGTTVTVSS |
| 11 | ELTQSPGTLSLSPGERATLSCRASQSVSSSYLAWYQQKPGQAPRLLIYG ASSRATGIPDRFSGSGSGTDFTLTISRLEPEDFAVYYCQQYGSSPRLTFG GGTKVEIK |
| 12 | EEIPLYYDSGYGMDV |
| 13 | ELTQSPVTLSLSPGERATLSCGASQSVSSSNLAWYQQKPGLAPRLLIYD ASSRATGIPDRFSGSGSGTDFTLTISRLEPEDFAVYYCQQYGSSLITFGQ GTRLEIK | a virus is elicited by the virus in its true and replicating form, while the immunization of an animal usually consists of the injection of a purified protein or of a non-replicating form of the virus. As a consequence, antibodies elicited in the natural host usually have a stronger activity and, being directed against conformational epitopes, are usually less subject to the emergence of viral escape mutants.

Therefore, an embodiment of the present invention is a combination comprising:

a) an HSV-1 and HSV-2 binding monoclonal antibody or a fragment thereof comprising both a heavy ($V_H$) and a light chain ($V_L$) variable region and a complementary determining region (CDR) chosen from the group consisting of SEQ ID NO: 3, SEQ ID NO: 6, SEQ ID NO: 9 and SEQ ID NO: 12 and b) and antiviral agent;

characterized in that the weight ratio between component a) and component b) is from 1000 to 0.01.

Preferably the weight ratio between component a) and component b) is from 100 to 0.1, more preferably from 10 to 0.1.

In a preferred embodiment the combination of the present invention is for sequential, simultaneous or separate administration.

In a further preferred embodiment of the present invention in the HSV-1 and HSV-2 binding monoclonal antibody or fragment thereof said heavy chain ($V_H$) variable region is selected from the group consisting of SEQ ID NO: 1, SEQ ID NO: 4, SEQ ID NO: 7 and SEQ ID NO: 10 or an homologous thereof.

According to the present invention holomogous of the heavy chain variable regions refer to sequences which preferably have at least 95% overall sequence similarity, homology or identity with said $V_H$ variable regions. Said homologous have at least 96%, 97%, 98% or 99% overall sequence similarity or homology.

In a further preferred embodiment of the present invention in the HSV-1 and HSV-2 binding monoclonal antibody or fragment thereof said light chain ($V_L$) variable region is selected from the group consisting of SEQ ID NO: 2, SEQ ID NO: 5, SEQ ID NO: 8 and SEQ ID NO: 11 or an homologous thereof.

According to the present invention holomogous of the light chain variable regions refer to sequences which preferably have at least 95% overall sequence similarity, homology or identity with said $V_L$ variable regions. Said homologous have at least 96%, 97%, 98% or 99% overall sequence similarity or homology.

Preferably, said antibody has a heavy chain ($V_H$) variable region of SEQ ID: 1 and a light chain ($V_L$) variable region of SEQ ID N: 2.

In a further preferred embodiment the HSV-1 and HSV-2 binding monoclonal antibody or fragment thereof has a IgG1 heavy chain constant region or a IgG2 heavy chain constant region.

Preferably said monoclonal antibody is a human antibody.

In a preferred embodiment of the present invention the antiviral agent is selected from Aciclovir, Penciclovir, Ganciclovir, Foscarnet, Ibacitabine, cidofovir, valganciclovir valacyclovir or famciclovir, preferably from Aciclovir, Penciclovir, Ganciclovir or Foscarnet.

A further embodiment is the combination according to the present invention for use as medicament.

A further embodiment is the use of the combination of the present invention in the treatment of herpes virus infections, selected from genital herpes, HSV gingivostomatitis and recurrent herpes labialis, herpes simplex encephalitis (HSE), neonatal HSV, HSV disease in the immunocompromised host and HSV keratitis or keratoconjunctivitis.

Preferably said herpes virus infections are HSV-1 and/or HSV-2 associated diseases. In a further embodiment the active principles of the combination according to the present invention can be administered simultaneously, separately or sequentially for use in the treatment of the HSV-1 and/or HSV-2 associated diseases. That is, the active principles of the combination of the invention can be administered simultaneously, separately or sequentially, also following different routes of administration for the each active principle and different times of administration for each active principle.

According to an embodiment, the combinations of the present invention are administered orally, rectally, parenterally or systemically.

In a further embodiment the active principles of the combination according to the present invention can be administered together, using the same routes of administration or using different routes of administration, otherwise they can be administered separately with the same routes of administration or with different routes of administration.

In a preferred embodiment the monoclonal antibody of the present invention or a fragment thereof is administered parenterally with a once a month injection and the antiviral agent is administered orally up to five times a day, for 30 days, preferably 10 to 15 days, more preferably one week.

In a preferred embodiment, the monoclonal antibody of the present invention or a fragment thereof is administered systemically in form of intramuscular, intravenous or subcutaneous injections at dosages ranging from 0.1 µg/Kg to 50 µg/Kg body weight, and the antiviral agent is administered orally at dosages ranging from 25 to 5000 mg, preferably from 100 to 2500 mg, more preferably from 250 to 2000 mg, or parenterally at dosages ranging from 1 to 100 mg/Kg body weight, preferably at dosages ranging from 5 to 50 mg/Kg body weight.

Preferably the monoclonal antibody or a fragment thereof is administered intramuscularly or subcutaneously at a dosage ranging from 1 µg/Kg to 15 µg/Kg body weight.

In a preferred embodiment of the present invention the antiviral agent is Aciclovir and it is administered orally in a dosage ranging from 1000 to 1600 mg daily, or parenterally in a dosage ranging from 5 to 10 mg/Kg body weight.

In a further preferred embodiment the antiviral agent is Valaciclovir and it is administered in a dosage ranging from 1000 to 2000 mg daily.

According to the present invention when the antiviral agent is Foscarnet, it is administered intravenously in a dosage ranging from 40 to 60 mg/Kg body weight, when it is Famciclovir or Penciclovir it is administered orally in a dosage ranging from 250 to 1000 mg daily, when it is Ganciclovir it is administered in a dosage ranging from 5 to 10 mg/Kg body weight.

In a further embodiment, the monoclonal antibody of the present invention or a fragment thereof is administered topically in form of a liquid or semisolid formulation, selected from solutions, suspensions, emulsions, gels, creams, ointments and the like.

In a preferred embodiment the antiviral agent is administered systemically in form of oral compositions or parenteral solutions.

In a further preferred embodiment the antiviral agent is administered topically in a form of a liquid or semisolid formulations, selected from solutions, suspensions, emulsions, gels, creams, ointments and the like.

In a further embodiment, both the monoclonal antibody or a fragment thereof and the antiviral agent may be administered in the same formulation systemically or topically.

Examples of those formulations may be injectable vials or topical formulations including solutions, suspensions, emulsions, gels, creams, ointments and the like.

The following examples are included to illustrate the invention, without the purpose to limit it.

Experimental Section

In the following experimental section we disclose the identification of the monoclonal antibodies which bind and neutralize HSV-1 and HSV-2. The procedure can be summarized as follows:

1. Analysis of the subjects' polyclonal sera;
2. Purification of the IgG2 fraction;
3. Evaluation of the quantity of IgG2 purified from the sera;
4. Evaluation of the IgG2 binding and neutralization activity towards HSV;
5. Subject selection;
6. IgG2 library construction from the selected subject;
7. Library validation and biopanning optimization;
8. Preliminary screening of the IgG2 antibody clones selected after the Fab production in Freezing and Thawing;
9. Fab IgG2 clone purification, sequencing and preliminary evaluation of neutralizing activity against HSV;
10. Conversion of the clones into Fab IgG1;
11. Purification and sequencing of the IgG1-transformed clones; exhaustive and quantitative evaluation of their neutralizing activity (the neutralizing activity was evaluated for all the clones, however an exhaustive and fine evaluation of the neutralizing activity was performed only for Fab-Ex2).

Subject Selection: Criteria and Results

IgG2 fractions were collected, detected and purified from peripheral blood samples deriving from a selected cohort of subjects.

The selection criteria were the following:

1) high content of IgG2, 2) capability to recognize HSV-1 and HSV-2 in ELISA assays, and 3) clinical history of HSV reactivation.

The serum from subject no. 18 was the only sample able to meet all the aforementioned first-selection criteria. The subject no. 18 reported a previous history of frequent reactivation of labial HSV with a recent and spontaneous clinical improvement.

Purification and Characterization of the IgG2 Fraction from the Selected Subject.

Given the high amount of IgG2 purified from subject no. 18 serum and its capability to recognize both HSV-1 and 2 in ELISA assays, this subject was selected to investigate the ability of his purified IgG2 to neutralize HSV-1 and 2 infections. The IgG2 fraction from donor no. 18 was purified using the protocol described below in the Materials and Methods section (IgG2 Purification and quantitation protocol).

TABLE 1

Clinical features of subject N. 18
Subject no. 18

| | |
|---|---|
| Age (yrs) | 37 |
| Sex | Male |
| Height (m) | 1.90 |
| Weight (Kg) | 95.5 |
| Previous and concomitant conditions | No |
| HSV 1 | Yes - Clinical diagnosis |

TABLE 1-continued

Clinical features of subject N. 18
Subject no. 18

| | |
|---|---|
| HSV 2 | No - Clinical diagnosis |
| Laboratory diagnosis of HSV | Not performed |
| Antiviral drug/s taken for HSV-1 | Acyclovir (by topical administration) |
| Description of clinical symptoms | Paraesthesia and pain before the onset of clinical manifestations followed by the typical labial symptoms (vesicular lesions followed by ulcers and crusts at the vermillion labial border). The clinical picture spontaneously improved over the last 6 months. |

The IgG2 fraction derived from subject no. 18 (pIgG2-18) showed an extraordinary neutralizing activity against both HSV-1 and HSV-2. In particular, pIgG2-18 neutralizing activity against HSV-1 and HSV-2 tested viruses was assessed and confirmed using both qualitative assays (syncytia formation evaluation through bright field phase contrast optical microscope and Immunofluorescence assay) and quantitative assays (plaque reduction assays and quantitative neutralizing activity evaluation through Indirect Immuno-Fluorescence, IIF).

Selection and Generation of Anti-HSV Human Monoclonal Antibody Fab Fragments Directed Against HSV-1 and HSV-2 Antigens and Sequence Characterization a. Phagemidic IgG2 Fab Library Construction from Selected Subject The subject no. 18 was selected as a B lymphocytes source due to the high neutralizing activity against HSV-1 and HSV-2 tested isolates, and the inhibition of syncytia formation in HSV-1 and HSV-2-infected VERO-E6 cells, shown by the IgG2 fraction purified from his serum.

A new blood sample was collected from subject no. 18 in order to isolate his B lymphocytes. After extracting and retrotranscribing mRNA from these cells, IgG2 HCs (heavy chains) and LCs (light chains) were cloned into a phagemidic vector (L Solforosi, et al. "A phage display vector optimized for the generation of human antibody combinatorial libraries and the molecular cloning of monoclonal antibody fragments" (2012) New Microbiologica 35 (3), 289-294.)

A human combinatorial phage displayed antibody library was obtained as described below in the Materials and Methods section.

b. Library Biopanning Conditions: Development of Biopanning Conditions Allowing Molecular Selection and Cloning of Anti-HSV Human Monoclonal Antibodies Able to Recognize and Neutralize Both HSV-1 and HSV-2

Cloning of human Fab fragments able to cross-recognize and neutralize both HSV-1 and HSV-2 was obtained by an optimized biopanning procedure that allowed the molecular cloning of human Fabs featuring such biological properties. The screening of the selection rounds was performed by Freeze & Thawing procedure as described below in the Materials and Methods section.

From this selection strategy, five human monoclonal IgG2 Fab fragments were generated, namely:

Fab Ex2: corresponding to SEQ ID NO.1 and SEQ ID NO.2; Fab

Ex2B: corresponding to SEQ ID NO.4 and SEQ ID NO.5; Fab

Ex2C: corresponding to SEQ ID NO.7 and SEQ ID NO.8; Fab

Ex2H: corresponding to SEQ ID NO.10 and SEQ ID NO.11; Fab

Ex2I: corresponding to SEQ ID NO.4 and SEQ ID NO.13.

These five monoclonal IgG2 Fab fragments were selected and tested in IIF against HSV-1 and HSV-2 infected cells. All the selected clones selectively recognized both HSV-1 and HSV-2 infected cells.

Production and Affinity Chromatography Purification of Selected IgG2 (G2) Fabs

The selected Fabs were produced in prokaryotic system and purified by affinity chromatography as described below in the Materials and Methods section.

Biological Activity Evaluation of Purified Selected Clones Directed Against HSV-1 and HSV-2

Purified Fabs (Ex2(G2), Ex2B(G2), Ex2C(G2), Ex2H (G2) and Ex2I (G2)) were pre-incubated (10 µg/mL) with a standard amount of HSV-1 or HSV-2 isolates. Appropriate experimental controls were also included. The different "infection-mix" was used to infect Vero E6 cells (adsorption 2 hours before change of medium).

After twenty hours, the cell monolayers were Fixed and Permeabilized with crystal violet containing solution allowing first a qualitative evaluation of Fabs biological activities against both HSV-1 and HSV-2 isolates (procedure described in the Materials and Methods section). The reduction of syncytia formation was assessed by bright field phase contrast optical microscopy. As already stated, this assay allowed a first evaluation of Fab potencies. All the Fabs showed a good neutralization activity against both HSV-1 and 2 isolates. Only Ex2C(G2) and Ex2H(G2), showed a lower potency against HSV-2 when compared to Ex2(G2) and the other Fabs.

Conversion of the IgG2 Selected Fab Fragments Directed Against Both HSV-1 and HSV-2 (Five Fabs) into IgG1 Fab, Expression and Production In order to optimize expression rate both in prokaryotic and eukaryotic (whole IgG1) production systems, all the selected IgG2-Fabs directed against both HSV-1 and HSV-2 were successfully converted into IgG1 Fabs. The variable regions on heavy chains (HCs) belonging to selected Fabs and LCs were successfully cloned into modified vector containing constant region (CH1) of IgG1 (procedures described in the Materials and Methods section). When not indicated, expressly or by (G2), the Fabs described in this patent are IgG2 Fabs converted to IgG1 as described.

All the procedures used to characterize the IgG2 selected Fabs were repeated to characterize the IgG1 form of selected Fabs allowing to compare the respective biological properties of IgG2 and IgG1 Fab formats.

From the biological activity assays, it was possible to demonstrate that IgG1 converted Fabs were still capable of recognizing and neutralizing both HSV-1 and 2 isolates with a high potency. Moreover, it was possible to show that the IgG1 format of Fab Ex2 neutralizes both HSV-1 and HSV-2 with an increased potency compared to its original clone format.

The biological assays performed are listed below:

Syncytia Formation Evaluation: Qualitative Assays Performed in Order to Evaluate Activity of Fab Clones of IgG1 Format Directed Against HSV-1 and HSV-2

The qualitative assays (described in the Materials and Methods section) were performed on IgG1 format of selected anti-HSV-1 and 2 Fabs (FIG. 11). These assays showed that also IgG1 formats of selected Fabs were able to neutralize both HSV-1 and HSV-2 (Table 2).

TABLE 2

Results of qualitative assays performed on IgG1 format of selected Fabs.

| Fab (IgG1) | HSV-1 | HSV-2 |
|---|---|---|
| Ex2 | ++++ | +++++ |
| Ex2B | ++ | ++ |
| Ex2C | ++ | +/− |
| Ex2H | ++ | + |
| Ex2I | + | +++ |

Quantitative Assays Performed with Anti-HSV-1 and 2 Neutralizing Fabs (IgG1 Format).

These assays were performed to quantify the potency of the selected anti-HSV Fab panel. All the Fab biological activities against HSV-1 and 2 were first assessed by IIF analysis.

The neutralizing activity of Fabs Ex2, Ex2B, Ex2C, Ex2H and Ex2I was evaluated using the InCellAnalyzer automated count system in order to calculate the IC50s of all Fab and obtain a dose-response curve. Several dilutions of the different Fabs were used in order to obtain the dose-response curve. In all sets of neutralization experiments several Fab dilutions were performed since only using a biological compound limit dilution was possible to obtain the exact amount of Fab able to inhibit viral infection.

Moreover, the same "dose-response" curve allowed the calculation of Fab IC50 which effectively depicts the in vitro Fab potency. The IC50 is the Fab concentration able to reduce by 50% the cell damage due to the infection of cell monolayer with a standard amount of virus (HSV-1 and HSV-2).

In other words, a low IC50 means that a very low amount of Fab is needed to inhibit the viral infection (data not shown).

The IC50 of Fab Ex2 is summarized below:

TABLE 3

IC50 of Fab Ex2.

| Fab | HSV-1 ($IC_{50}$ µg/mL ± CI 95%) | HSV-2 ($IC_{50}$ µg/mL ± CI 95%) |
|---|---|---|
| Ex2 | 0.7 (0.44 ± 1.21) | 0.2 (0.19 ± 0.23) |

Exhaustive Study of IgG1 Fab Ex2 Neutralizing Activity

Fab Ex2 showed the most promising results against HSV-1 and HSV-2.

In order to further characterize and confirm its biological activity several neutralization experiments were performed following the procedures described below in the Materials and Methods section.

Qualitative Neutralizing Activity Evaluation Through Syncytia Formation Assay

This assay shows the effective potency of the Fab allowing to evaluate the presence/absence of cytopathic effects (complete disruption of cellular morphology) in the presence or absence of Fab Ex2.

In order to evaluate the potency of Fab Ex2, a qualitative assay using different dilutions was performed. Three different concentrations of Ex2 (10 µg/ml, 5 µg/ml and 2.5 µg/ml) were tested against HSV-1 and 2 through the syncytia formation assay.

Fab Ex2 was able to strongly inhibit the cellular disruption and syncytia formation caused HSV-1 infection in a dose-dependent manner, and to completely inhibit HSV-2 infection at very low concentrations.

When Fab Ex2 was added in different concentrations to the same infecting dose of HSV-1 or 2 prior to infection of the cell monolayer, the cellular morphology disruption was clearly inversely proportional to the Fab Ex2 concentration.

Gene usage analysis performed using a reference database of immunoglobulin sequences (IMGT), allowed a preliminary examination of the mutational rate of the selected clones compared to their germ-line sequences (Table 4).

All the selected Fab clones are mutated in their CDRs (Complementarity Determining Regions) when compared to the respective germ-line sequences. This means that the different clones display unique somatic mutations matured after the contact with the antigens.

This usually allows more specific antigen recognition.

TABLE 4

| Fab Sequence ID | Functionality | V-GENE and allele | V-REGION identity % |
|---|---|---|---|
| HCs | | | |
| Ex2 | productive | Homsap IGHV3-30-3*01 F | 94.1 |
| Ex2B | productive | Homsap IGHV1-46*01 F, or Homsap IGHV1-46*03 F | 91.0 |
| Ex2C | productive | Homsap IGHV3-23*01 F, or Homsap IGHV3-23*04 F or Homsap IGHV3-23D*01 F | 89.9 |
| Ex2H | Productive | Homsap IGHV1-2*02 F | 89.6 |
| Ex2I | Productive | Homsap IGHV1-46*01 F, or Homsap IGHV1-46*03 F | 91.0 |
| LCs | | | |
| Ex2 | Productive | Homsap IGKV3D-7*01 F | 80.5 |
| Ex2B | Productive | Homsap IGKV3-20*01 F | 91.5 |
| Ex2C | Productive | Homsap IGKV3D-20*01 F | 93.6 |
| Ex2H | Productive | Homsap IGKV3-15*01 F | 93.2 |
| Ex2I | Productive | Homsap IGKV3D-20*01 F | 93.6 |

The extremely good results observed for Fab Ex2 with the inhibition of syncytia formation assays, are consistent with the quantitative evaluation of Fab A neutralization potency described below.

Quantitative Neutralizing Activity Evaluation Through Plaque Reduction Assay

Dose-response quantitative assay: the capability of Fab Ex2 to inhibit HSV infection was assessed by evaluating the presence of lysis plaques on cell monolayer due to HSV infection in the presence or in the absence of Fab Ex2. To confirm the IIF neutralization data, a plaque reduction assay was performed as quantitative evaluation.

As widely described in the literature, the plaque assay is considered as the experiment of choice for the in vitro evaluation of neutralizing activity against HSV infection and is currently the gold standard for the evaluation of mAb IC50.

The dose-dependent quantitative evaluation of the biological activity of Fab Ex2 against HSV-1 and 2, not only endorsed the qualitative results previously described, but also showed that Fab Ex2 potency was unexpectedly high. In fact, as clearly shown in the graph, even at a very low concentration (1 µg/mL) Fab Ex2 inhibited HSV-1 plaque formation measured as PFU (plaque-forming unit). In addition, the HSV-1 neutralization assay showed the Fab Ex2 dose-response effect, as already evidenced by the qualitative dose-dependent assays.

Due to the very high potency of Fab Ex2, a dose-response effect could not be measured by the neutralization assay carried out with the HSV-2 isolate.

Sequence Study and Gene Usage Analysis of Selected Fab Clones

The sequences of both HCs and LCs from selected Fabs revealed that all the chains are correctly on frame and without any stop codon that can affect their expression level.

Conversion of the IgG1 Fab Ex2 into a Full IgG1, Identified as IgGA

Single Chain Antibody A (ScFvA) Production and Evaluation

ScFv gene of IgGA was successfully constructed and cloned into expression vector. ScFv format small scale production of IgGA was performed. The binding activity of ScFv A was evaluated by IIF assays on HSV infected cells. The ScFv A was able to recognize HSV infected cells. However, ScFv A showed high IIF background signal and low binding.

Fab Ex2: corresponds to SEQ ID NO.1 and SEQ ID NO.2

In Vitro Evaluation of the Biological Activity of IgGA

Neutralising Activity Against Clinical Isolates

The neutralising activity of FabA or IgGA was evaluated by pre-incubating (1 h at 37° C.) the IgGA with the virus and adding the IgGA/virus-mixture to cell monolayer.

Results

IgG A potently neutralises all the tested HSV-1 and 2 tested isolates. Importantly, the HSV isolates used to perform the neutralisation assays were endowed with different susceptibility to Acyclovir (ACV) anti-HSV drug. The capability of IgGA to neutralise the aforementioned HSV isolates indicates that the IgGA extraordinary biological activity is totally independent from the susceptibility to ACV showed by the different HSV tested isolates, suggesting a possible use of IgGA for the treatment of HSV infections caused by ACV resistant isolates.

Evaluation of Post Adsorption Inhibition of Infection

Post-adsorption assays have been developed in order to speculate on possible administration of IgGA for the treatment of HSV infection, after the beginning of virus active replication within the host.

The first step of experimental approaches, involving post-HSV adsorption evaluation of FabA or IgGA, is the infection of VERO E6 cells with a standard amount of HSV not previously treated with the FabA or IgGA.

FabA or IgGA is added to the infected cells only after 30 minutes from virus infection. The infection is then carried out for 48 h in order to appreciate the HSV lysis plaques on VERO E6 cells. The experimental results have been evaluated by counting the plaques for infected cells receiving (post-HSV infection) FabA or IgGA compared to virus experimental positive control.

Fabs tested in post-adsorption assays have been used at a concentration of 50 and 200 ug/mL against HSV-1 and HSV-2 tested isolates respectively*.

IgGs tested in post-adsorption assays have been used at a concentration of 25 and 100 ug/mL against HSV-1 and HSV-2 tested isolates respectively*.

* mAb concentrations inferred from scientific literature

Results

As demonstrated by post-adsorption assays, IgGA strongly inhibits both for HSV-1 and HSV-2 new infection events and also inhibits the number of infectious foci resulting in plaques compared to virus controls. IgGA inhibition strength was higher than those observed with FabA (FIG. 15B).

Cell-to-Cell Infection Mechanism Inhibition

Among the HSV infection strategies, an important one is the so called "cell-to-cell" infection strategy.

Post post-adsorption assays have been performed in order to evaluate the contribution of IgGA in inhibiting "cell-to-cell" infection by measuring the plaque areas resulting from infected cells treated or untreated with FabA or IgGA.

Fabs tested in post-adsorption cell-to-cell infection inhibition assays have also been preliminary used at a concentration of 50 and 200 ug/mL against HSV-1 and HSV-2 tested isolates respectively*.

IgGs tested in post-adsorption "cell-to-cell" infection inhibition assays have also been preliminary used at a concentration of 25 and 100 ug/mL against HSV-1 and HSV-2 tested isolates respectively*.

* mAb concentrations inferred from scientific literature

Results

As demonstrated by post-adsorption assays, Fab A inhibits both for HSV-1 and HSV-2 the plaque areas. IgGA inhibition of plaque areas is even higher than Fab A inhibition activity. These data clearly demonstrated how IgGA post-infection administration can potently inhibit also "cell-to-cell" HSV infection.

Evaluation of the Emergence of Escape Mutants Under Selective Pressure of mAbA

In order to evaluate the presence of escape virus mutants generated under selective pressure of IgGA, HSV-1 infected VERO-E6 cells have been treated with increasing concentrations of Fab A. More in details, VERO cells have been cultured in T25 flasks in the experimental conditions extensively described in the previous reports ("virus propagation techniques"). Cell monolayers have been then infected by HSV-1 HF strain using 50 pfu/mL of cell free virus. After virus complete adsorption, the infected cells have been treated for three days with 0.2 ug/mL and 1 ug/mL of IgGA. Experimental controls, unrelated IgG (at concentration of 0.2 ug/mL and 1 ug/mL) and virus "alone" have been also included in the experiments. After three days the infected cell media have been collected and centrifuged in order to use medium centrifuged supernatants for new cell infection rounds. These new infection rounds have been carried out in the presence of 0.2 ug/mL and 1 ug/mL of IgGA and experimental controls. Five sequential identical infection rounds have been performed in the presence of the two concentrations of IgGA and control IgG above described. The cell supernatants of the last infection round have been then centrifuged and used to perform five new round of infection in the presence of increased concentrations of IgGA (5 ug/mL and 10 ug/mL). In order to test the capability of virus cultured in the constant presence of IgGA to escape from IgGA inhibitory activity the cell free supernatants belonging to the final infections in the presence of IgGA have been incubated 1 h at 37° C. in the presence of high IgGA concentration. After pre-incubation the neutralization mix has been used to infect new VERO-E6 cells.

Results

The IgGA pre-incubated with HSV has been still able to neutralize the virus isolate indicating that no "escape mutants" have been generated under the IgGA selective pressure at 5 and 10 ug/mL.

This indicates that: HF HSV-1 isolates tested in these experiments very hardly undergo amino acid mutations in the region recognized by our antibody allowing its escape from the antiviral activity of IgGA (in the presence of the two concentration of IgGA used to perform the assays).

Conclusions

No "escape mutants" were generated under the IgGA selective pressure. Possible explanations of this result can be summarized as follows: HF HSV-1 isolates tested in these experiments do not easily undergo amino acid mutations allowing its escape from the antiviral activity of IgGA (in the presence of the two concentrations of IgGA used to perform the assays).

Materials and Methods Section

Eukaryotic Cells and Viruses

VERO-E6 cell line were—used to perform all the experimental procedures on eukaryotic cells HSV-1 isolate cultured on VERO-E6 cells: HF strain (VR-260 ATCC)

HSV-2 isolate cultured on VERO-E6 cells: MS strain (VR-540 ATCC)

ELISA for IgG2 Fraction Detection Protocol:

Microtiter 96-wells flat bottom ELISA plates (COSTAR) were coated (overnight at 4° C.) with the collected sera PBS diluted including a negative control.

Nonspecific sites were blocked by incubating the plate (37° C. for an hour) with 1% PBS/BSA solution.

After washing (PBS solution containing 0.2% (v/v) Tween20 (Sigma-Aldrich)), the commercially available mouse anti-Human IgG2 specific monoclonal antibody was added following the manufacturer instructions protocol (1 hour at 37° C.)

Washing with PBS solution containing 0.2% (v/v) Tween20

Peroxidase-conjugated anti-mouse IgG (Sigma-Aldrich) was added (45' at 37° C.)

After washing with PBS solution containing 0.2% (v/v) Tween20, TMB substrate kit (Thermo Scientific) was added and the plate incubated at 37° C. for 5'

1N sulphuric acid was then added to stop the reaction.

The signal was detected at 450 nm wavelength.

Western Blot for IgG2 Fraction Detection Protocol:

The collected sera were analysed on 8% Tris-glycine gels (Bio-Rad) at two different dilutions (1:10 and 1:100 respectively).

Proteins were transferred to PVDF membrane (PerkinElmer) for 15 hours at 30V at 4° C.

Nonspecific sites were blocked by incubating the membrane over night at 4° C. in a PBS solution containing 0.2% (v/v) Tween20 (Sigma-Aldrich) and 5% (w/v) non fat dried milk.

The commercially available mouse mAb specific for human IgG2 was used as a primary reagent for 1 hour incubation at room temperature.

Washing with a PBS solution containing 0.1% (v/v) Tween20.

The blot was probed with peroxidase-conjugated anti-mouse IgG (Sigma-Aldrich) (45' at room temperature).

The peroxidase-conjugated Ab was detected using the Super Signal West Pico Chemiluminescent Substrate (Thermo Scientific).

ELISA Assay Against HSV-1 and HSV-2 Coated Inactivated Viruses

Microtiter 96-wells flat bottom ELISA plates (COSTAR) were coated (overnight at 4° C.) with heat-inactivated HSV-1 and HSV-2 ECB diluted (1:10) including a negative control.

Nonspecific sites were blocked by incubating the plate (37° C. for an hour) with 1% PBS/BSA solution.

After washing (PBS solution containing 0.2% (v/v) Tween20 (Sigma-Aldrich)), the collected sera PBS/BSA diluted (1:200) was added (1 hour at 37° C.)

Washing with PBS solution containing 0.2% (v/v) Tween20

Peroxidase-conjugated anti-human IgG (Sigma-Aldrich) was added (45' at 37° C.)

After washing with PBS solution containing 0.2% (v/v) Tween20, TMB substrate kit (Thermo Scientific) was added and the plate incubated at 37° C. for 5'

1N sulphuric acid was then added to stop the reaction.

The signal was detected at 450 nm wavelength.

IgG2 Purification and Quantitation Protocol:

In order to purify and analyze the IgG2 fraction, the selected sera were purified using two different steps. Firstly, the total amount of IgG was purified with an affinity column. Secondly, the eluted total IgG content was further purified with an affinity column specific for IgG2 fraction.

a) Preparation of Total IgG Affinity Purification Column: Column 1 Preparation Protocol 1 mL of gammabind Sepharose resin (stored at 4° C. in PBS1x-ethanol 20%) was washed 3 times with 30-40 mL PBS1x to eliminate the ethanol excess (centrifuge 5 min at 2500 rpm at room temperature and 2-3 acceleration and deceleration).

Anti-human IgG (Cf=4 mg/mL) was added to the resin and gently stirred 90 min at room temperature.

The resin was washed 3 times with 10 volumes (1 volume=1 mL of resin) of sodium borate 0.2M pH 9. Centrifuge 15 min at 2500 rpm.

After the first centrifuge, the supernatant was recovered for further analysis.

The resin was resuspended in 10 volumes of sodium borate 0.2 M pH 9 and shacked.

A small amount of beads was removed for pre cross-linking checking.

DMP (dimethyl-pimelimidate) was added up to 20 mM (final concentration). In this step takes place the cross-linking between IgGs and protein G of the resin. Stir gently 30 min at room temperature.

A small amount of beads was removed for post cross-linking checking.

After 15 min centrifuge (2500 rpm), the supernatant was removed and the resin was washed with 20 volumes of ethanolamine 0.2M pH 8.

This step was repeated 3 times. This step allows the stabilization of new covalent links.

The resin was then washed with 20 volumes of ethanolamine (0.2M pH 8) and stirred gently for 120 min at room temperature.

After 15 min centrifuge (2500 rpm), the supernatant was removed and the resin was washed 3 times with 30 mL PBS1x.

After 15 min centrifuge (2500 rpm), the supernatant was removed and 20 mL of PBS1x supplemented with NaN3 (final concentration 0.05%) were added.

The resin was finally loaded on the chromatography column and then stored at 4° C.

b) Preparation of IgG2 Fraction Affinity Purification Column: Column 2 Preparation Protocol The protocol for the preparation of total IgGs-affinity purification column above described was used to prepare a new column allowing the purification of the IgG2 fraction. A single modification was performed in the protocol (second step of the Column 1 preparation protocol above described).

In particular:

A commercially available mouse anti-Human IgG2 Fc monoclonal antibody (Acris Antibodies) was added to the resin at the final concentration of 3 mg/mL and gently stirred for 90 min at room temperature.

c) Affinity Purification Procedure: Column 1/Column 2 Steps

The collected sera were firstly purified in the "Column no. 1" (total IgG purification column). Briefly, after incubating the different sera at room temperature, the column was washed with PBS1x allowing the elution of nonspecific serum proteins. The IgG fraction was then eluted by changing the pH of the column (pH 2.2).

After elution the total IgG containing solution was neutralized (pH 7.0) and loaded again into the "Column no. 2" (IgG2 fraction purification column). As described for Column 1 purification, the Column 2 eluted samples, were neutralized and stored at 4° C. to be further analysed.

d) Evaluation of the Purified IgG2

The affinity columns above described allowed the purification of IgG2 from human sera. In order to evaluate the quality of the samples purified, SDS-PAGE assays, followed by Coomassie staining were-performed:

The samples were analysed on 4-15% Tris-glycine pre-casted-gels (Bio-Rad).

Electrophoresis run was performed for 1 hour at 200V.

The electrophoresis gels were stained for 20 min with a Coomassie-blue solution.

The Coomassie-stained gels were washed in Destainer-containing solution for 2 hours and then washed with tap clean water.

Syncytia Formation Evaluation Through Bright Field Phase Contrast Optical Microscope Protocol:

$10^4$ Vero cells/well were grown till a 100% confluence in a 96-well plate in complete DMEM+10% FCS.

HSV-1 and HSV-2 viral stocks dilutions (−3 and −2 respectively) were pre-incubated with purified Fab of interest at different concentrations (10, 5 and 2.5 µg/mL) in a final volume of 100 µL of complete DMEM, for 1 h at 37° C. and 5% $CO_2$.

Experimental controls were added as well.

After washing the cells with a PBS 1x solution, viral solutions were added to the monolayers and incubated for 2 h at 37° C. and 5% $CO_2$ for adsorption.

Each well was washed once in PBS 1x, then complete DMEM supplemented with 2% FCS were added to each well and incubated for 22 h at 37° C. and 5% $CO_2$.

Cells monolayer were fixed and stained with 1 mL of a water-based solution of 70% methanol and 1% crystal violet.

The fixing/staining solution was removed after 5' incubation, and then the cells monolayer was washed once in $H_2O$ and dried.

The reduction of syncytia formation was assessed by bright field phase contrast optical microscope. In particular, the cell morphology observed in the cell monolayer infected with Fab or IgG1 Fab-treated viruses was compared with the virus control (same virus amount without purified IgG2) infected cells morphology.

Qualitative Immunofluorescence (IIF) Assay Protocol:

$10^4$ Vero cells/well were grown till a 100% confluency in a 96-well plate in complete DMEM+10% FCS.

Cells were infected with the same HSV-1 and HSV-2 viral stocks dilution used in neutralization assay, then adsorption and incubation were performed as previously described for viral titration.

Medium was removed, the cells monolayer was washed once in PBS 1× and fixed with 200 µL/well of a 1:1=acetone:methanol ice-cold solution. Fixing solution was removed. The plate was stored at −20° C.

The IIF staining was performed by adding anti-HSV-1 and HSV-2 gD2 protein mAbs commercially available (1 h 37° C. in dark humid chamber)

The plate was washed twice (5' in PBS1×)

A FITC-conjugated secondary mAb was added to the primary staining (1 h 37° C. in dark humid chamber)

The plate was washed twice (5' in PBS1×)

The nuclear staining was performed by adding Hoechst solution (15 min 37° C. in dark humid chamber)

The plate was washed twice (5' in PBS1×)

The infection foci were analysed through InCellAnalyzer system.

Quantitative Neutralizing Activity Evaluation Through Plaque Reduction Assay Protocol:

$7×10^5$ Vero cells/well were seeded in a 6-wells plate and grown in the appropriate complete medium supplemented with 10% FCS. Experiment was performed with cells at 100% confluence.

HSV-1 and HSV-2 viral stocks dilution (−5 and −4 respectively) were pre-incubated with purified Fab of interest at different concentrations (5, 2.5 and 1 µg/mL) in a final volume of 800 µL of complete DMEM, for 1 h at 37° C. and 5% $CO_2$.

Experimental controls were added as well.

After washing the cells with a PBS 1× solution, viral solutions were added to the monolayers and incubated for 2 h at 37° C. and 5% $CO_2$ for adsorption.

Each well was washed once in PBS 1×, then 2 mL of complete DMEM supplemented with 2% FCS and 1% agarose were added to each well and incubated for 46 h at 37° C. and 5% $CO_2$.

Agarose layer was removed and cells monolayer fixed and stained with 1 mL of a water-based solution of 70% methanol and 1% crystal violet. Fixing/staining solution was removed after a 5' incubation, then the cells monolayer was washed once in PBS 1× and dried.

Neutralization activity was then assessed by counting the plaque forming units (PFU). In particular, the number of PFU in the cell monolayer infected with Fab-treated viruses was compared with the PFU counted for the virus control (same virus amount).

Quantitative Neutralizing Activity Evaluation Through Indirect Immunofluorescence (IIF) Assay Protocol:

$10^4$ Vero cells/well were grown till a 100% confluence in a 96-well plate in complete DMEM+10% FCS.

HSV-1 and HSV-2 viral stocks dilution (−4 and −2 respectively) were pre-incubated with purified Fab of interest at different concentrations in a final volume of 100 µL of complete DMEM, for 1 h at 37° C. and 5% $CO_2$.

Experimental controls were added as well.

After washing the cells with a PBS 1× solution, viral solutions were added to the monolayers and incubated for 2 h at 37° C. and 5% $CO_2$ for adsorption.

Each well was washed once in PBS 1×, then complete DMEM supplemented with 2% FCS were added to each well and incubated for 22 h at 37° C. and 5% $CO_2$.

Medium was removed, the cells monolayer was washed once in PBS 1× and fixed with 200 µL/well of a 1:1=acetone:methanol ice-cold solution. Fixing solution was removed. The plate was stored at −20° C.

The IIF staining was performed by adding anti-HSV-1 and HSV-2 mAbs commercially available (1 h 37° C. in dark humid chamber)

The plate was washed twice (5' in PBS1×)

A FITC-conjugated secondary mAb was added to the primary staining (1 h 37° C. in dark humid chamber)

The plate was washed twice (5' in PBS1×)

The nuclear staining was performed by adding Hoechst solution (15 min 37° C. in dark humid chamber)

The plate was washed twice (5' in PBS1×)

Neutralization activity was then assessed by counting the immunofluorescence infection foci through InCellAnalyzer system.

The number of infection foci in the cell monolayer infected with viruses treated with the different Fab preparations was compared with the foci counted for the virus control (same virus amount)

The percentage of neutralization was then evaluated and a standard deviation from the mean was calculated as well (the experiment was performed in triplicate)

Human Combinatorial Phage Displayed Antibody Library Construction Protocol:

PBMCs (peripheral blood mononuclear cells) were separated from a blood sample using Histopaque 1077 (Sigma), a Ficoll gradient solution designed for blood cell separation.

RNA was extracted from the isolated lymphocytes using Rneasy Mini Kit (Qiagen), and was retrotranscribed to cDNA using the Transcriptor 1st Strand cDNA Synthesis Kit for RT-PCR AMV (Roche), following the product manual instructions.

Previously obtained cDNA was-used as PCR template. In particular, using a specific set of primers described by Solforosi et al. (2012) "A phage display vector optimized for the generation of human antibody combinatorial libraries and the molecular cloning of monoclonal antibody fragments" New Microbiologica 35 (3), 289-294, the amplification of light (LC) and heavy chains (HC) of immunoglobulins belonging to IgG2 subclass was performed (see Supplementary 1 section for primer sequences).

All the amplified HC and LC were-purified after electrophoresis agarose gel "run" using QIAquick Gel extraction Kit, (Qiagen). After the purification step both chains were-also quantified (NanoDrop 8000, Higher throughput, full-spectrum microvolume UV-Vis measurements, ThermoScientific) and digested with selected restriction enzymes (as highlighted by the next two tables explaining the enzymatic digestion reaction mix) to clone them into the pCM vector (Solforosi et al. (2012) "A phage display vector optimized for the generation of human antibody combinatorial libraries and the molecular cloning of monoclonal antibody fragments" New Microbiologica 35 (3), 289-294), following the protocol already described.

More in detail, LCs and pCM were-digested with SacI and XbaI restriction enzymes (NEB) following the protocol shown in Table 5:

TABLE 5

| LC digestion | |
|---|---|
| LCs | Vector |
| LCs 5 µg | pCM vector 10 µg |
| SacI 35 U/µg | SacI 5 U/µg |
| XbaI 70 U/µg | XbaI 9 U/µg |
| Buffer 10X | Buffer 10X |
| BSA | BSA |

The digestions were-carried out for 45 min (vector) and 3 hours (LCs) respectively at 37° C. and the digested products were then checked through Sybr Safe staining.

Digested pCM and LC DNA showing the correct molecular weight (3500 and 670 bps respectively) were extracted from agarose gel, purified (QIAquick Gel extraction Kit, Qiagen), and subsequently ligated (2 hours at room temperature) using T4 DNA ligase (NEB). The ligation product was-then used to transform electrocompetent cells (*E. coli* XL-1 Blue electrocompetent cells, Stratagene).

pCM containing LCs (pCMLc) was then purified (Qiagen Plasmid Midi Kit, Qiagen) from the transformed cells.

pCMLc vector and the previously amplified HCs were also digested, as explained in the next table showing the digestion conditions.

XhoI and SpeI restriction enzymes (NEB) were used, as follows in Table 6.

TABLE 6

| HC digestion | |
|---|---|
| HCs | pCMLc |
| HCs 5 µg | Vector 10 µg |
| XhoI 70 U/µg | XhoI 9 U/µg |
| SpeI 17 U/µg | SpeI 3 U/µg |
| Buffer 10X | Buffer 10X |
| BSA | BSA |

The digestions were carried out for 45 min (vector) and 3 hours (HCs) respectively at 37° C. and the digested products were then checked through Sybr Safe staining (FIG. 10).

Digested pCMLc and HC DNA showing the correct molecular weight (4000 and 730 bps respectively) were extracted from agarose gel, purified (QIAquick Gel extraction Kit, Qiagen), and subsequently ligated (2 hours at room temperature) using T4 DNA ligase (NEB). The ligation product was then used to transform "homemade" XL-1 Blue electrocompetent cells.

pCM containing LCs and HCs (pCMLcHc) was-then purified (Qiagen Plasmid Midi Kit, Qiagen) from the transformed cells.

Biopanning Protocol:

Day 1

Transform an aliquot of XL1-Blue electrocompetent cells with library DNA

After a recovery of 60' at 37° C. with agitation in 2 mL SOC medium (2% Tryptone, 0.5% Yeast extract, 10 mM NaCl, 2.5 mM KCl, 10 mM MgCl2, 10 mM MgSO$_4$, and 20 mM Glucose), add it to 10 mL SB medium (3.2% Tryptone, 2% Yeast extract, 0.5% Sodium chloride—pH: 7.0±0.2) with 10 µg/mL Tetracycline and 20 µg/mL Ampicillin ("Low Amp")

Library Titration: plate on Tet-Amp agar plates serial dilutions starting from $10^{-2}$ to $10^{-5}$ Incubate Low Amp for 60' at 37° C. with agitation Add 50 mL SB medium with 100 µg/mL Ampicillin ("High Amp") and incubate for 60' at 37° C. with agitation Add $10^{12}$ PFU (Plaque forming units: a measure of the number of particles capable of forming plaques per unit volume) of helper phage (homemade produced and titrated) and incubate for 60' at 37° C. with agitation Add 70 µg/mL Kanamycin and incubate overnight (ON) at 30° C.

Plate preparation for affinity selection of phages:

Vero E6 cells were seeded in a Costar™ 96-Well EIA/RIA Plate, $4 \times 10^4$ cells/well in DMEM+10% FBS, 4 wells for each infection, and incubated ON at 37° C., 5% CO$_2$. The following day HSV-1 (HF strain) stock was $10^{-2}$ diluted in DMEM without FBS and seeded on cells for 2 hours absorption. Then, the medium containing medium was replaced with DMEM+2% FBS and the plate was-incubated for 20 hours at 37° C., 5% CO2. The infected cells were fixed using 40 uL/well of paraformaldehyde solution (Invitrogen IC Fixation Buffer—FB001) for 15' at room temperature. After the incubation time, the solution was replaced with 100 µL/well of PBS.

Day 2

Calculate the phage titre of day 1 using the following formula: $10^4 \times$(dilution factor)$\times$(number of colonies)/µL on the plate Inoculate an XL1-Blue colony in SB with 10 µg/mL Tetracycline (4 mL for each antigen, 2 mL for infection with Output phages and 2 mL for infection with Input phages) and incubate at 37° C. with agitation until reaching an optical density (OD) of 0.5 at 550 nm wavelength Phage Preparation:

After centrifugation (40' at 4° C., RCF: 1540×g) of the ON bacterial culture growth, pour the supernatant into sterile 50 mL tubes with 8 mL of PEG/NaCl solution and incubate for 30' on ice allowing the phages precipitation.

After centrifugation (25' at 4° C., RCF: 12130×g), discard the supernatant and gently resuspend the pellet with 1 mL of PBS/BSA 1% solution.

After centrifugation (5' at room temperature, RCF: 21380×g), collect the supernatant ("Unpanned phage")

Deselection Process:

a suspension of Vero E6 cells obtained from a 100% confluent T75 flask was—fixed using 500 µL of paraformaldehyde solution (Invitrogen IC Fixation Buffer—FB001) for 15' at room temperature. After the incubation time, the cells were washed in PBS solution. Before adding the resuspended phage to the plate containing the treated HSV infected cells (selection step), the phage solution was pre-incubated with $1.5 \times 10^6$ cells/well for 60' at 37° C. with agitation (deselection step). After centrifugation (2' at room temperature, RCF: 21380×g), the supernatant was then collected and added to the plate with the fixed and permeabilized HSV infected cells.

Panning:

Incubate 70 µL/well of unpanned phage for 120' at 37° C.

Collect the supernatant from the 4 wells of each antigen as "Input" and store on ice Wash every well 10 times with 100 µL/well of PBS/Tween 0.5% solution at 37° C., pipetting 10 times each Add 50 µL/well of Elution Buffer (0.1 M Glycine-HCl, pH 2.2), incubate 1' and scrape off the bottom of the wells Collect the eluted phages with Neutralizing Buffer (2 M Tris, pH 8.0) as "Output" and store on ice Usually five selection rounds (six days) are needed in order to obtain a high affinity selection of clones with a significant antigen-binding activity from the phage population obtained from a DNA library of Fabs.

Importantly, a cross-selection of phage antibody library on HSV-1 and HSV-2 infected cells on the first panning selection round was performed.

Screening Protocol Using Freeze & Thawing Procedure:
Day 1:
Extract DNA obtained from High Amp of rounds 4 and 5 and double digest with SpeI and NheI restriction enzymes (NEB) for 60' at 37° C.

Separate the DNA of interest (the plasmid containing both HCs and LCs) from the phage protein (cpIII) previously fused to the Fabs, performing an agarose 1% gel electrophoresis run (85V for 3 hours) and extract with the QIAquick Gel Extraction Kit (QIAgen)

Ligate the extracted DNA using T4 ligase (NEB) and transform an aliquot of XL1-Blue elettrocompetent cells
After recovery in SOC medium, plate on LB agar
Day 2:
Inoculate colonies obtained on day 1 in 3 mL SB medium with 10 µg/mL Tetracycline and 100 µg/mL Ampicillin for each one. Add a colony of not transformed XL1-Blue elettrocompetent cells in 3 mL SB medium with only 10 µg/mL tetracycline as negative control. Incubate the inoculates at 37° C. with agitation until reaching an optical density (OD) of 0.5 at 550 nm wavelength Induce the production of Fabs adding IPTG (Isopropyl β-D-1-thiogalactopyranoside—Sigma I6758) at the recommended dilution of 1:1000 and incubate ON at 30° C. with agitation
Day 3:
After centrifugation (20' at 4° C., RCF: 1540×g) of the ON bacterial cultures growth, discard supernatant and resuspend the pellet with 1 mL of PBS.

Add a protease inhibitor and follow the Freeze&thaw procedure for three times:
Incubate on dry ice until complete freezing
Incubate at 37° C. with agitation until complete thawing
After centrifugation (10' at room temperature, RCF: 21380×g), use the supernatant for protein (Fab) expression screening and the pellet for DNA extraction and analysis.

Purification of Fab Clones Selected During Biopanning Procedures Protocol:
Day 1
Inoculate a fresh plate colony in 10 mL SB (Super Broth) containing 10 µL ampicillin (Cf=50 µg/mL, C. stock=100 mg/mL) and 20 µL tetracycline (Cf=100 µg/mL, C. stock=5 mg/mL) and incubate overnight at 37° C. in a rotatory shaker (180 rpm)
Day 2
Sub-inoculate 5 mL of the inoculum into 500 mL SB (Super Broth) containing 500 µL ampicillin (Cf=50 µg/mL, C. stock=100 mg/mL) and 1 mL tetracycline (Cf=100 µg/mL, C. stock=5 mg/mL) and incubate at 37° C. for 6-8 hours in a orbital shaker (180 rpm)

When the culture OD reach 0.8-1 (exponential growth) add IPTG (isopropyl-b-D-thiogalactopyranoside) at a final concentration of 1 mmol/L
Incubate overnight at 30° C. in a orbital shaker (180 rpm)
Day 3
Transfer the bacterial culture in clean 250 mL bottles.
Centrifuge (20-30' at 3500-4500 rpm) at 4° C. or room temperature.

Resuspend cellular pellet in a final volume of 25 mL of PBS1× into falcon 50 mL, add protease inhibitors and place the falcon at 4° C.

Maintaining the falcon on ice, sonicate cellular suspension 90", pause 60". Repeat this 3-4 times.

Transfer the bacterial lysate in bottle (30 mL). Eliminate cell debris by centrifugation for 30' at 15.000 rpm at 4° C.

Filter the supernatant using syringe 50 ml and filters Millipore PVDF from 0.45 um and then from 0.2 um. Collect the filtrate into falcon 50 mL.
Store at 4° C.
Purify the Fab by immunoaffinity chromatography:
Wash the column with 20 mL PBS1×. Repeat twice
Elution with 10 mL Elution Buffer pH 2.2
Rebalance the pH of the column with PBS1×, check the pH
Close column cap. Load on the column sample, 2-4 mL at a time. Wait few minutes and reopen the column
Wash the column with 50 mL PBS1×
Close column cap. Load on the column 10 mL Elution Buffer pH 2.2, 2-4 mL at a time. Wait few minutes and reopen the column.
Collect the eluate in falcon containing Neutralising Buffer pH 11
Check the pH and neutralise the solution (pH 7-8) using Neutralising Buffer pH 11
Rebalance the pH of the column with PBS1×
Elution with 10 mL Elution Buffer pH 2.2
Rebalance the pH of the column with PBS1×, check the pH
Add 20 mL PBS1×+200 µL NaN3100× and store the column at 4° C.
Wash Centricon with PBS1×: centrifuge 10-15' at 4000 rpm. Then, concentrate Fab with centrifugation for 10-15' at 4000 rpm.
Take the Fab purified retained by the filter and store at 4° C.

The correct expression and the concentration of purified Fabs were calculated respectively by SDS-PAGE/coomassie staining (as already described in IgG2 Purification and quantitation protocol).

Conversion of IgG2 Fab Fragments into IgG1 Fab Protocol

This cloning procedure was-performed using the pCM vector (Solforosi et al. (2012) "A phage display vector optimized for the generation of human antibody combinatorial libraries and the molecular cloning of monoclonal antibody fragments" New Microbiologica 35 (3), 289-294) already containing HC and LC sequences of an IgG1 antibody. A NheI restriction site was introduced between the VH and CH1 sequences of the aforementioned IgG1-Fab allowing the molecular cloning of only the VH fragment of the HC.

The VH sequences of selected anti-HSV Fabs were-cloned in frame with IgG1-CH1.

More in details, a NheI restriction site was added at 3' end of selected Fab VH sequences by PCR amplification using specific designed primers containing the restriction site.

All the amplified VH were purified using QIAquick PCR Purification Kit, (Qiagen). After the purification step VH chains were also quantified (NanoDrop 8000, Higher throughput, full-spectrum microvolume UV-Vis measurements, ThermoScientific) and digested with selected restriction enzymes to clone them into the expression vector, following the protocol already described.

More in detail, both amplified VHs and vector were digested with XhoI and NheI restriction enzymes (NEB) following the protocol of Table 7:

TABLE 7

| VHs | IgG1 Ab Vector |
| --- | --- |
| VH 0.5 µg | Vector 5 µg |
| XhoI 10 U/µg | XhoI 10 U/µg |
| NheI 10 U/µg | NheI 10 U/µg |
| Buffer cutsmart 10X | Buffer cutsmart 10X |

The digestions were carried out for 1 hour at 37° C. and the digested products were then checked through Sybr Safe staining.

Digested products showing the correct molecular weight (4474 bp for VH-digested vector and 426 bps for VHs) were extracted from agarose gel, purified (QIAquick Gel extraction Kit, Qiagen), and subsequently ligated (10 minutes at room temperature) using T4 DNA ligase (NEB). The ligation product was then used to transform electrocompetent cells (E. coli XL-1 Blue electrocompetent cells, Stratagene).

Plasmids containing VHs ligated in frame with IgG1-CH1 (pVH-CH1-IgG1) were then purified (Qiagen Plasmid Midi Kit, Qiagen) from the transformed cells and the correct insertion was analysed sequencing the portion of interest with a specific subset of primers.

pVH-CH1-IgG1 constructs and the LCs belonging to HSV Fab panel were also digested as explained in Table 8 showing the digestion conditions.

TABLE 8

| LCs | pVH-CH1-IgG1 |
| --- | --- |
| LC 0.5 µg | Vector 2 µg |
| SacI 10 U/µg | SacI 10 U/µg |
| XbaI 10 U/µg | XbaI 10 U/µg |
| Buffer cutsmart 10X | Buffer cutsmart 10X |

The digestions were carried out for 1 hour at 37° C. and the digested products were then checked through Sybr Safe staining.

Digested pVH-CH1-IgG1 and LC DNAs showing the correct molecular weight (4230 and 670 bps respectively) were extracted from agarose gel, purified (QIAquick Gel extraction Kit, Qiagen), and subsequently ligated (10 minutes at room temperature) using T4 DNA ligase (NEB). The ligation product was then used to transform XL-1 Blue electrocompetent cells (Stratagene). Plasmids containing LCs and HCs of the different anti-HSV clones (pVH-CH1_LC-IgG1Fab) were—then purified (Qiagen Plasmid Midi Kit, Qiagen) from the transformed cells and the correct insertion was analysed sequencing the portion of interest with a specific subset of primers.

As described in the cloning protocol paragraph, all the new IgG1 Fab clones were sequenced in order to check the correct insertion of VH-HCs and LCs.

ScFvA Construction

In order to extensively characterise mAb A (or Ex2) features in its different formats, the mAb has been also expressed as a single chain antibody A (ScFvA).

Variable light chain (VL) and variable heavy chain (VH) of Fab A have been amplified and used for the construction of a single chain (ScFv).

The ScFv gene cassette is composed by:
a) DNA encoding for Fab A VL and VH
b) DNA encoding for a linker region [(Glyx3Ser)x3]
c) DNA encoding protein tag (Poly-Histidine)

The ScFv Fab A (Fab Ex2) gene cassette has been constructed as follows:

a) DNA Encoding for Fab A VL and VH

As stated above, the Fab A variable regions for the Light and Heavy chains (VL and VH respectively) have been successfully amplified by PCR (polymerase chain reaction) from the DNA template encoding for mAb A light and heavy variable regions. The primers used to amplify mAb A LC and HC from DNA template contained:

At 5' VL end the restriction site SacI (New England Biolabs, NEB) to be used for the insertion of the whole ScFv gene cassette into vector.

At 3' VL end the part of the DNA sequence encoding for the linker region (linker overlap region)

At 5' VH part of the DNA sequence encoding for the linker region (linker overlap region)

At 3' VH the DNA sequence coding for the His Tag and the restriction site SpeI (NEB) to be used for the insertion of the whole ScFv gene cassette into expression vector.

All the gene fragments amplified as above described have been used to perform overlap PCRs in order to construct the full length ScFv gene cassette b) DNA Encoding for a Linker Region [(Glyx$_3$Ser)x$_3$]

The linker region (in between LC and HC) main function is structural, in particular a linker region composed by [(Gly)$_3$Ser]$_3$ is characterised by high flexibility allowing a proper ScFv folding after expression. The linker region has been added in between the VL and VH by PCR overlap techniques.

c) DNA Encoding Protein Tag (Poly-Histidine)

Poly-Histidine Tag region (His-Tag) is fundamental for the ScFv purification by affinity chromatography. In particular, this region is selectively bound by Ni2+ NiNta resin (commercially available, QIAGEN) routinely used to purify His-Tag containing proteins. His-Tag DNA sequence has been added to ScFv gene cassette introducing Poly-His DNA coding sequence into 3'VH primer already containing the Spe I restriction site.

The gene cassette has been then cloned vector and ScFvA has been produced, using the following protocol:

1. Transformation of bacteria (XL-1 Blue, Stratagene) with ScFv containing vector XL-1 Blue bacteria have been transformed (by elettroporation) with vector containing the ScFv A gene cassette.

2. Selective culturing of bacteria containing the ScFv vector

XL1 Blue bacteria correctly transformed with ScFv vector have been cultured and selected with antibiotic (ampicillin) thanks to the amp$^r$ (ampicillin resistance gene) resistance marker carried by the vector.

3. ScFv expression induction

The expression of ScFv A has been induced by adding the so called "inductor" (IPTG) to the culture broth containing ScFv transformed bacteria 4. Cultured bacteria sonication In order to collect the ScFv produced by bacteria after the induction step, ScFvA expressing bacteria have been sonicated to disrupt bacterial wall and release ScFvA produced by bacteria.

5. Centrifugation of cell free supernatant to pellet cellular debris. Sonicated bacteria product, has been extensively centrifuged in order to pellet bacterial cell debris.

6. Ni$^{2+}$ affinity chromatography purification

Supernatants resulting from step 5, have been collected and loaded into Ni2+ affinity chromatography column in order to purify the ScFv thanks to His-Tag.

7. ScFv collection

Purified ScFv has been then collected and stored at −20° C.

EXAMPLES

Example 1

Evaluation of the Emergence of Escape Mutants Under Selective Pressure of IgGA

VERO-E6 monolayers were infected with HSV-1 HF strain using 50 pfu/mL of cell free virus. After virus complete adsorption, the infected cells were treated for three days with subinhibitory concentrations of IgGA, namely 0.2 mg/ml and 1 mg/ml.

Experimental controls were unrelated IgG (at concentrations of 0.2 mg/ml and 1 mg/ml) or no treatment. After three days, the infected cell media were collected, centrifuged and the supernatants used for new cell infection rounds, for a total of 5 sequential rounds. Cell supernatants of the last infection round were centrifuged and used to perform five new rounds of infection in the presence of higher concentrations of IgGA (5 mg/ml and mg/ml). The cell free supernatants belonging to the final infection round were incubated 1 h at 37° C. in the presence of high IgGA concentrations and then used to infect new VERO-E6 cells.

Results obtained demonstrated that IgGA pre-incubated with HSV were still able to neutralise the virus isolates, indicating that no "escape mutants" were generated under the IgGA selective pressure at 5 and 10 mg/ml.

Example 2

Evaluation of Synergistic Activity of IgGA and Acyclovir

To investigate the synergistic activity of IgGA and Acyclovir (ACV), different concentrations of Acyclovir and IgGA were tested in combination in a double curve assay in vitro.

Briefly, different IgGA concentrations (0, 1, 10, 25, 50 µg/ml) were combined with different ACV concentrations (0, 0.25, 0.5, 1 µg/ml) and added to VERO E6 cells, 30 min after HSV infection. After 48 h of incubation the infected cells were stained with Crystalviolet/EtOH and plaques of lysis counted. Results show that IgGA combined with Acyclovir can significantly increase the inhibitory effects of Acyclovir at the different concentrations tested (FIG. 1).

Results obtained in the double curve assay were then analysed in silico in a ComboSyn analysis (CompuSyn for Drug Combinations and for General Dose-Effect Analysis by Ting-Chao Chou Memorial Sloan-Keltering Cancer Center New York, N.Y. and Nick Martin Massachustts Institute of Technology Cambridge, Mass.) to evaluate the potential synergies between IgGA and ACV, through the calculation of Combination Index (CI) and Dose Reduction Index (DRI).

The combination index (CI) according to Chou 2006 (23) indicates nearly additive activity in the range of 0.9-1.1, synergism under 0.9, strong synergism between 0.1 and 0.3 and very strong synergism under 0.1. Values of CI over 1.1 indicate antagonism.

CI calculation demonstrated that all combinations of IgGA with ACV resulted in synergistic activity (FIGS. 2 and 3). Results obtained in this experiment demonstrated synergism in the combination of moderate to high amounts of IgGA with low doses of ACV, suggesting a promising potential use of ACV at lower concentrations especially in those patients suffering for ACV kidney toxicity.

In addition, the dose reduction index (DRI) results indicate a very favourable dose reduction for both IgGA and Acyclovir (FIG. 4).

In the following examples the evaluation of synergistic activity of IgGA previously observed for IgGA/ACV mixtures, has been extended also to other anti-herpetic drugs such as FOS (Foscarnet), PCV (Penciclovir) and GCV (Ganciclovir). Importantly the synergistic activity has been evaluated against both HSV-1 and HSV-2 infected cells using the in house optimised post-virus entry inhibition assays mimicking in vitro the capability of mAb/drug mixtures to reduce virus dissemination and cell damage when used after virus infection.

Example 3

Evaluation of Synergistic Activity of IgGA and Foscarnet

In order to test the possible use of IgGA in combination with anti-HSV drug Foscarnet (FOS), IgGA/FOS combinations have been tested in post-HSV entry assays (assays performed at 37° C. allowing virus entry).

The first step in IgGA/FOS combination activity evaluation has been the assessment of drug susceptibility for the two chosen HSV isolates already used for the Example 2. The FOS concentrations chosen to perform synergistic assays FOS/mAbs have been 0.5, 25 and 100 mg/ml against HSV-1 LV and 5, 10 and 25 mg/ml against HSV-2 MS. Combination index was calculated as in Example 2 to assess the synergism between IgGA and FOS.

CI: combination index

The combination index calculation demonstrated that all except one combinations of IgGA with FOS resulted in synergistic activity against HSV-1 tested isolate, as only a single drugs combination showed a CI>1 (FIG. 5). Moreover, synergism could be reached by using moderate to high amounts of IgGA in combination with low doses of FOS, suggesting a possible use of FOS at low concentrations for those patients suffering for FOS toxicity.

The combination index calculation demonstrated that all but three combinations of IgGA with FOS resulted in synergistic activity against the HSV-2 tested isolate (FIG. 6). Moreover, strong synergism could be reached by using high amounts of IgGA in combination with low doses of FOS, indicating also against HSV-2 infection a possible use of low concentrations of FOS. In this regard, it is important to point out that 70% of inhibition of HSV-2 infection has been achieved by combining a dose of IgGA approximately corresponding to IgGA MIC50 (ED50) and a nearly ineffective dose of FOS (0.5 ug/mL).

Example 4

Evaluation of Synergistic Activity of IgGA and Penciclovir

In order to test the possible use of IgGA in combination with anti-HSV drug Penciclovir (PCV), several assays have been performed. Importantly, as well as for experiments above described, combinations have been tested in post-HSV entry assays.

The first step in IgGA/PCV combination activity evaluation has been the assessment of drug susceptibility for the two chosen HSV isolates (HSV-1 LV and HSV-2 MS). PCV concentrations chosen to perform synergistic assays PCV/mAbs have been: 0.5, 0.75 and 1.5 µg/mL against HSV-1 LV and 1.5, 2.5 and 7 µg/mL against HSV-2 MS. Combination index was calculated as in Example 2 to assess the synergism between IgGA and PCV.

CI: combination index

The combination index calculation demonstrated that all combinations of IgGA with PCV resulted in synergistic activity against HSV-1 (FIG. 7). One combination resulted in strong synergism. High levels of synergism could be reached by using moderate to high amounts of IgGA in combination with low doses of PCV, indicating a possible therapeutic use of PCV at lower concentrations against HSV-1.

The combination index calculation from mAbA/PCV "combo" activity against HSV-2 demonstrated that almost all combination of IgGA with PCV resulted in synergistic activity: one very strong and three strong synergism; only two drugs combinations showed a CI>1 (FIG. 8).

Example 5

Evaluation of Synergistic Activity of IgGA and Ganciclovir

In order to test the possible use of IgGA in combination with anti-HSV drug Ganciclovir (GCV), several assays have been performed. Importantly, as well as for experiments above described, combinations have tested in post-HSV adsorption assays.

The first step in IgGA/GCV combination activity evaluation has been the assessment of drug susceptibility for the two chosen HSV isolates. In detail, HSV-1 LV and HSV-2 MS have been selected as they have been already used for synergism studies. GCV concentrations chosen to perform synergistic assays GCV/mAbs were: 0.05, 0.25 and 0.75 mg/ml against HSV-1 LV and 0.01, 0.1 and 0.5 mg/ml against HSV-2 MS. Combination index was calculated as per the Example 2.

CI: combination index

The combination index calculation demonstrated that all except one combination of IgGA with GCV resulted in synergistic activity against HSV-1 (FIG. 9). A single drug combination showed a CI>1. Moreover, it has been possible to identify different synergistic levels for the different drug combos, with four of them classified as very strong synergism. However, this effect could be reached by using moderate to high amounts of IgGA in combination with the highest tested dose of GCV.

The combination index obtained for HSV-2 demonstrated that the majority of combinations of IgGA with GCV resulted in synergistic activity (FIG. 10), indicating a possible use of GCV at low concentrations especially in those patients suffering from GCV toxicity.

REFERENCES

1. Bradley H, Markowitz L E, Gibson T, et al. Seroprevalence of herpes simplex virus types 1 and 2—United States, 1999-2010. J Infect Dis 2014; 209:325-33.
2. Ryder N, Jin F, McNulty A M, et al. Increasing role of herpes simplex virus type 1 in first-episode anogenital herpes in heterosexual women and younger men who have sex with men, 1992-2006. Sex Transm Infect 2009; 85:416-9.
3. Roberts C M, Pfister J R, Spear S J. Increasing proportion of herpes simplex virus type 1 as a cause of genital herpes infection in college students. Sex Transm Dis 2003; 30:797-800. 4. Bernstein D I, Bellamy A R, Hook E W, 3rd, et al. Epidemiology, clinical presentation, and antibody response to primary infection with herpes simplex virus type 1 and type 2 in young women. Clin Infect Dis 2013; 56:344-51
5. 2015 STD Treatment Guidelines, Center for Disease Control and Prevention
6. Leone P A, Trottier S, Miller J M. Valacyclovir for episodic treatment of genital herpes: a shorter 3-day treatment course compared with 5-day treatment. Clin Infect Dis 2002; 34:958-62.
7. Wald A, Carrell D, Remington M, et al. Two-day regimen of acyclovir for treatment of recurrent genital herpes simplex virus type 2 infection. Clin Infect Dis 2002; 34:944-8.
8. Aoki F Y, Tyring S, Diaz-Mitoma F, et al. Single-day, patient-initiated famciclovir therapy for recurrent genital herpes: a randomized, double-blind, placebo-controlled trial. Clin Infect Dis 2006; 42:8-13.
9. Chosidow O, Drouault Y, Leconte-Veyriac F, et al. Famciclovir vs. aciclovir in immunocompetent patients with recurrent genital herpes infections: a parallel-groups, randomized, double-blind clinical trial. Br J Dermatol 2001; 144:818-24.
10. Bodsworth N J, Crooks R J, Borelli S, et al. International Valaciclovir HSV Study Group. Valaciclovir versus aciclovir in patient initiated treatment of recurrent genital herpes: a randomised, double blind clinical trial. Genitourin Med 1997; 73:110-6.
11. Fife K H, Barbarash R A, Rudolph T, et al. The Valaciclovir International Herpes Simplex Virus Study Group. Valaciclovir versus acyclovir in the treatment of first-episode genital herpes infection: results of an international, multicenter, double-blind, randomized clinical trial. Sex Transm Dis 1997; 24:481-6.
12. Diaz-Mitoma F, Sibbald R G, Shafran S D, et al. Collaborative Famciclovir Genital Herpes Research Group. Oral famciclovir for the suppression of recurrent genital herpes: a randomized controlled trial. JAMA 1998; 280:887-92.
13. Mertz G J, Loveless M O, Levin M J, et al. Collaborative Famciclovir Genital Herpes Research Group. Oral famciclovir for suppression of recurrent genital herpes simplex virus infection in women: a multicenter, double-blind, placebo-controlled trial. Arch Intern Med 1997; 157:343-9.
14. Reitano M, Tyring S, Lang W, et al. International Valaciclovir HSV Study Group. Valaciclovir for the suppression of recurrent genital herpes simplex virus infection: a large-scale dose range-finding study. J Infect Dis 1998; 178:603-10.
15. Romanowski B, Marina R B, Roberts J N, et al. Patients' preference of valacyclovir once-daily suppressive therapy versus twice-daily episodic therapy for recurrent genital herpes: a randomized study. Sex Transm Dis 2003; 30:226-31.
16. Corey L, Wald A, Patel R, et al. Once-daily valacyclovir to reduce the risk of transmission of genital herpes. N Engl J Med 2004; 350:11-20.
17. Goldberg L H, Kaufman R, Kurtz T O, et al. Acyclovir Study Group. Long-term suppression of recurrent genital herpes with acyclovir: a 5-year benchmark. Arch Dermatol 1993; 129:582-7.
18. Fife K H, Crumpacker C S, Mertz G J, et al. Acyclovir Study Group. Recurrence and resistance patterns of herpes simplex virus following cessation of years of chronic suppression with acyclovir. J Infect Dis 1994; 169:1338-41
19. Brown Z A, Wald A, Morrow R A, et al. Effect of serologic status and cesarean delivery on transmission rates of herpes simplex virus from mother to infant. JAMA 2003; 289:203-9.

20. Brown Z A, Benedetti J, Ashley R, et al. Neonatal herpes simplex virus infection in relation to asymptomatic maternal infection at the time of labor. N Engl J Med 1991; 324:1247-52.
21. Pinninti S G, Angara R, Feja K N, et al. Neonatal herpes disease following maternal antenatal antiviral suppressive therapy: a multicenter case series. J Pediatr 2012; 161: 134-8.
22. Krawczyk A(1), Arndt M A, Grosse-Hovest L, Weichert W, Giebel B, Dittmer U, Hengel H, Jager D, Schneweis K E, Eis-Hubinger A M, Roggendorf M, Krauss J. Overcoming drug-resistant herpes simplex virus (HSV) infection by a humanized antibody. Proc Natl Acad Sci USA. 2013 23; 110(17):6760-5.
23. Chou T C. Theoretical basis, Experimental Design, and Computerized simulation of synergism and Antagonism in Drug combination Studies. Pharmacological Reviews. 2006; 58(3): 621-681.

The invention claimed is:

1. A combination containing:
   a) an HSV-1 and/or HSV-2 binding monoclonal antibody or a fragment thereof comprising both a heavy ($V_H$) and a light chain ($V_L$) variable region, wherein:
   i) said $V_H$ comprises the complementary determining regions (CDRs) contained within the $V_H$ sequence of SEQ ID NO: 1, including the CDR of SEQ ID NO: 3, and said $V_L$ comprises the CDRs contained within the $V_L$ sequence of SEQ ID NO: 2;
   ii) said $V_H$ comprises the CDRs contained within the $V_H$ sequence of SEQ ID NO: 4, including the CDR of SEQ ID NO: 6, and said $V_L$ comprises the CDRs contained within the $V_L$ sequence of SEQ ID NO: 5;
   iii) said $V_H$ comprises the CDRs contained within the $V_H$ sequence of SEQ ID NO: 7, including the CDR of SEQ ID NO: 9, and said $V_L$ comprises the CDRs contained within the $V_L$ sequence of SEQ ID NO: 8;
   iv) said $V_H$ comprises the CDRs contained within the $V_H$ sequence of SEQ ID NO: 10, including the CDR of SEQ ID NO: 12, and said $V_L$ comprises the CDRs contained within the $V_L$ sequence of SEQ ID NO: 11; or
   v) said $V_H$ comprises the CDRs contained within the $V_H$ sequence of SEQ ID NO: 4, including the CDR of SEQ ID NO: 6, and said $V_L$ comprises the CDRs contained within the $V_L$ sequence of SEQ ID NO: 13; and
   b) an antiviral agent selected from Aciclovir, Penciclovir, Ganciclovir, or Foscarnet;
   characterized in that the weight ratio between component a) and component b) is from 1000 to 0.01.

2. The combination according to claim 1 characterized in that the weight ratio between component a) and component b) is from 100 to 0.01.

3. The combination according to claim 1, wherein component a) and component b) are for sequential, simultaneous or separate administration.

4. The combination according to claim 1, characterized in that said heavy chain ($V_H$) variable region is selected from the group consisting of SEQ ID NO: 1, SEQ ID NO: 4, SEQ ID NO: 7 and SEQ ID NO: 10 or a homolog of any thereof, wherein the homolog has at least 96% overall sequence similarity, homology or identity with the relevant $V_H$ region, provided said homolog comprises the CRDs of the relevant $V_H$ region as defined in claim 1.

5. The combination according to claim 1, characterized in that said light chain ($V_L$) variable region is selected from the group consisting of SEQ ID NO: 2, SEQ ID NO: 5, SEQ ID NO: 8 and SEQ ID NO: 11 or a homolog of any thereof, wherein the homolog has at least 96% overall sequence similarity, homology or identity with the relevant $V_L$ region, provided said homolog comprises the CDRs of the relevant $V_L$ region as defined in claim 1.

6. The combination according to claim 1 characterized in that the HSV-1 and/or HSV-2 binding monoclonal antibody or fragment thereof has a IgG1 heavy chain constant region or a IgG2 heavy chain constant region.

7. A method for the treatment of herpes virus infections selected from genital herpes, HSV gingivostomatitis and recurrent herpes labialis, herpes simplex encephalitis (HSE), neonatal HSV, HSV disease in the immunocompromised host and HSV keratitis or keratoconjunctivitis in a patient, the method comprising administering to said patient a combination containing:
   a) an HSV-1 and/or HSV-2 binding monoclonal antibody or a fragment thereof comprising both a heavy ($V_H$) and a light chain ($V_L$) variable region, wherein:
   i) said $V_H$ comprises the complementary determining regions (CDRs) contained within the $V_H$ sequence of SEQ ID NO: 1, including the CDR of SEQ ID NO: 3, and said $V_L$ comprises the CDRs contained within the $V_L$ sequence of SEQ ID NO: 2;
   ii) said $V_H$ comprises the CDRs contained within the $V_H$ sequence of SEQ ID NO: 4, including the CDR of SEQ ID NO: 6, and said $V_L$ comprises the CDRs contained within the VL sequence of SEQ ID NO: 5;
   iii) said $V_H$ comprises the CDRs contained within the $V_H$ sequence of SEQ ID NO: 7, including the CDR of SEQ ID NO: 9, and said $V_L$ comprises the CDRs contained within the $V_L$ sequence of SEQ ID NO: 8;
   iv) said $V_H$ comprises the CDRs contained within the $V_H$ sequence of SEQ ID NO: 10, including the CDR of SEQ ID NO: 12, and said $V_L$ comprises the CDRs contained within the $V_L$ sequence of SEQ ID NO: 11; or
   v) said $V_H$ comprises the CDRs contained within the $V_H$ sequence of SEQ ID NO: 4, including the CDR of SEQ ID NO: 6, and said $V_L$ comprises the CDRs contained within the $V_L$ sequence of SEQ ID NO: 13; and
   b) an antiviral agent selected from Aciclovir, Penciclovir, Ganciclovir, or Foscarnet;
   characterized in that the weight ratio between component a) and component b) is from 1000 to 0.01.

8. The method according to claim 7, characterized in that the monoclonal antibody or a fragment thereof is administered systemically in the form of intramuscular, intravenous or subcutaneous injections at dosages ranging from 0.1 µg/Kg to 50 µg/Kg body weight, and the antiviral agent is administered orally at dosages ranging from 25 to 5000 mg, or parenterally at dosages ranging from 1 to 100 mg/Kg body weight.

9. The method according to claim 7, characterized in that the monoclonal antibody or a fragment thereof is administered topically in form of a liquid or semisolid formulations selected from solutions, suspensions, emulsions, gels, creams, ointments and the like.

10. The method according to claim 7, characterized in that the antiviral agent is administered systemically in the form of oral composition or parenteral solution.

11. The method according to claim 7, characterized in that the antiviral agent is administered topically in the form of liquid or semisolid formulation, selected from solutions, suspensions, emulsions, gels, creams, ointments and the like.

12. The method according to claim 7, characterized in that the monoclonal antibody or a fragment thereof and the antiviral agent are administered in the same formulation systemically or topically.

13. The method according to claim 7, characterized in that the monoclonal antibody or a fragment thereof is administered systemically in the form of intramuscular, intravenous or subcutaneous injections at dosages ranging from 0.1 µg/Kg to 50 µg/Kg body weight, and the antiviral agent is administered orally at dosages ranging from 100 to 2500 mg, or parenterally at dosages ranging from 5 to 50 mg/Kg body weight.

14. The method according to claim 7, characterized in that the monoclonal antibody or a fragment thereof is administered systemically in form of intramuscular, intravenous or subcutaneous injections at dosages ranging from 0.1 µg/Kg to 50 µg/Kg body weight, and the antiviral agent is administered orally at dosages ranging from 250 to 2000 mg, or parenterally at dosages ranging from 5 to 50 mg/Kg body weight.

15. The combination according to claim 1 characterized in that the weight ratio between component a) and component b) is from 10 to 0.1.

* * * * *

```
                       SEQUENCE LISTING

<160> NUMBER OF SEQ ID NOS: 13

<210> SEQ ID NO 1
<211> LENGTH: 113
<212> TYPE: PRT
<213> ORGANISM: Homo sapiens

<400> SEQUENCE: 1

Leu Glu Ser Gly Gly Gly Val Val Gln Pro Gly Arg Ser Leu Arg Leu
1               5                   10                  15

Ser Cys Ala Ala Ser Gly Phe Thr Phe Thr Thr Phe Ala Met His Trp
            20                  25                  30

Val Arg Gln Ala Pro Gly Lys Gly Leu Glu Trp Leu Ala Phe Ile Ser
        35                  40                  45

Tyr Asp Gly Ser Asn Lys Tyr Tyr Ala Asp Ser Val Lys Gly Arg Phe
    50                  55                  60

Thr Ile Ser Arg Asp Asn Ser Lys Asn Thr Leu Tyr Leu Gln Met Asn
65                  70                  75                  80

Ser Leu Arg Ala Glu Asp Thr Ser Ile Tyr Tyr Cys Ala Arg Glu Val
                85                  90                  95

Trp Asn Tyr Ala Asp Tyr Trp Gly Gln Gly Ala Leu Val Thr Val Ser
            100                 105                 110

Ser

<210> SEQ ID NO 2
<211> LENGTH: 106
<212> TYPE: PRT
<213> ORGANISM: Homo sapiens

<400> SEQUENCE: 2

Glu Leu Thr Gln Ser Pro Gly Thr Leu Ser Ser Ser Pro Gly His Arg
1               5                   10                  15

Ala Thr Leu Ser Cys Lys Ala Ser Ala Pro Leu Gly Ser Asn His Met
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Val Pro Ala Arg Phe Thr Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ala Asn Ser Phe Pro Arg Thr
                85                  90                  95

Phe Gly Gln Gly Thr Lys Val Glu Ile Lys
            100                 105

<210> SEQ ID NO 3
<211> LENGTH: 8
<212> TYPE: PRT
```

<213> ORGANISM: Homo sapiens

<400> SEQUENCE: 3

Glu Val Trp Asn Tyr Ala Asp Tyr
1               5

<210> SEQ ID NO 4
<211> LENGTH: 118
<212> TYPE: PRT
<213> ORGANISM: Homo sapiens

<400> SEQUENCE: 4

Leu Glu Gln Ser Gly Ala Glu Val Lys Lys Pro Gly Ala Ser Val Arg
1               5                   10                  15

Val Ser Cys Gln Ala Ser Gly Tyr Thr Phe Thr Asn Tyr Tyr Ile His
                20                  25                  30

Trp Val Arg Gln Ala Pro Gly Gln Gly Leu Glu Trp Met Gly Ile Ile
            35                  40                  45

Asn Pro Thr Gly Gly Ser Thr Arg Ile Ala Gln Lys Phe Gln Gly Arg
    50                  55                  60

Val Thr Met Thr Ser Asp Thr Ser Thr Ser Thr Ile Phe Met Glu Val
65                  70                  75                  80

Ser Ser Leu Arg Ser Glu Asp Thr Ala Ile Tyr Tyr Cys Ala Arg Asp
                85                  90                  95

Glu Tyr Lys Ser His His Tyr Gly Met Asp Val Trp Gly Gln Gly Thr
            100                 105                 110

Thr Val Thr Val Ser Ser
        115

<210> SEQ ID NO 5
<211> LENGTH: 107
<212> TYPE: PRT
<213> ORGANISM: Homo sapiens

<400> SEQUENCE: 5

Glu Leu Thr Gln Ser Pro Gly Thr Leu Ser Leu Ser Pro Gly Glu Arg
1               5                   10                  15

Ala Thr Leu Ser Cys Arg Ala Asn Glu Ser Val Ser Arg Ser Tyr Leu
                20                  25                  30

Ala Trp Tyr Gln Gln Arg Pro Gly Gln Ala Pro Arg Leu Leu Ile Tyr
            35                  40                  45

Gly Ala Ser Thr Arg Ala Thr Gly Ile Pro Ala Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln His Phe Gly Ser Ser Thr Gly Leu
                85                  90                  95

Thr Phe Gly Gly Gly Thr Lys Val Glu Ile Arg
            100                 105

<210> SEQ ID NO 6
<211> LENGTH: 12
<212> TYPE: PRT
<213> ORGANISM: Homo sapiens

<400> SEQUENCE: 6

Asp Glu Tyr Lys Ser His His Tyr Gly Met Asp Val
1               5                   10

<210> SEQ ID NO 7
<211> LENGTH: 120
<212> TYPE: PRT
<213> ORGANISM: Homo sapiens

<400> SEQUENCE: 7

Leu Glu Ser Gly Gly Gly Leu Val Gln Pro Gly Gly Ser Leu Arg Leu
1               5                   10                  15

Ser Cys Ala Ala Ser Gly Leu Pro Phe Asn Tyr Tyr Ala Met Asn Trp
            20                  25                  30

Val Arg Gln Ala Pro Gly Lys Gly Leu Glu Trp Val Ser Gly Ile Ser
        35                  40                  45

Ala Asn Gly Leu Asn Thr Tyr Tyr Ala Glu Ser Val Lys Gly Arg Phe
    50                  55                  60

Thr Ile Ser Arg Glu Asn Ser Gln Asn Thr Leu Tyr Leu Gln Met Asn
65                  70                  75                  80

Ser Leu Gly Ala Glu Asp Thr Ala Val Tyr Tyr Cys Ala Lys Val Leu
                85                  90                  95

Val Ala Ala Thr His Tyr Tyr Asn Gly Met Asp Val Trp Gly Gln
            100                 105                 110

Gly Thr Thr Val Thr Val Ser Ser
            115                 120

<210> SEQ ID NO 8
<211> LENGTH: 106
<212> TYPE: PRT
<213> ORGANISM: Homo sapiens

<400> SEQUENCE: 8

Glu Leu Thr Gln Ser Pro Val Thr Leu Ser Leu Ser Pro Gly Glu Arg
1               5                   10                  15

Ala Thr Leu Ser Cys Gly Ala Ser Gln Ser Val Ser Ser Ser Asn Leu
            20                  25                  30

Ala Trp Tyr Gln Gln Lys Pro Gly Leu Ala Pro Arg Leu Leu Ile Tyr
        35                  40                  45

Asp Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Leu Ile Thr
                85                  90                  95

Phe Gly Gln Gly Thr Arg Leu Glu Ile Lys
            100                 105

<210> SEQ ID NO 9
<211> LENGTH: 15
<212> TYPE: PRT
<213> ORGANISM: Homo sapiens

<400> SEQUENCE: 9

Val Leu Val Ala Ala Thr His Tyr Tyr Tyr Asn Gly Met Asp Val
1               5                   10                  15

<210> SEQ ID NO 10
<211> LENGTH: 121
<212> TYPE: PRT
<213> ORGANISM: Homo sapiens

<400> SEQUENCE: 10

Leu Glu Glu Ser Gly Ala Glu Val Lys Lys Pro Gly Ala Ser Val Arg
1               5                   10                  15

Val Ser Cys Lys Ala Ser Gly Tyr Thr Phe Thr Gly Tyr Phe Ile His
            20                  25                  30

Trp Val Arg Gln Ala Pro Gly Gln Gly Leu Glu Trp Met Gly Trp Ile
        35                  40                  45

Asn Pro Lys Ser Gly Gly Thr Asn Tyr Ala Pro Lys Phe Gln Gly Arg
    50                  55                  60

Val Thr Met Thr Arg Asp Thr Ser Ile Ser Thr Ala Tyr Met Gln Leu
65                  70                  75                  80

Ser Ser Val Arg Ser Asp Asp Thr Ala Val Tyr Tyr Cys Ala Arg Glu
                85                  90                  95

Glu Ile Pro Leu Tyr Tyr Asp Ser Gly Tyr Gly Met Asp Val Trp Gly
            100                 105                 110

Pro Gly Thr Thr Val Thr Val Ser Ser
        115                 120

<210> SEQ ID NO 11
<211> LENGTH: 107
<212> TYPE: PRT
<213> ORGANISM: Homo sapiens

<400> SEQUENCE: 11

Glu Leu Thr Gln Ser Pro Gly Thr Leu Ser Leu Ser Pro Gly Glu Arg
1               5                   10                  15

Ala Thr Leu Ser Cys Arg Ala Ser Gln Ser Val Ser Ser Ser Tyr Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Pro Arg Leu
                85                  90                  95

Thr Phe Gly Gly Gly Thr Lys Val Glu Ile Lys
            100                 105

<210> SEQ ID NO 12
<211> LENGTH: 15
<212> TYPE: PRT
<213> ORGANISM: Homo sapiens

<400> SEQUENCE: 12

Glu Glu Ile Pro Leu Tyr Tyr Asp Ser Gly Tyr Gly Met Asp Val
1               5                   10                  15

<210> SEQ ID NO 13
<211> LENGTH: 106
<212> TYPE: PRT
<213> ORGANISM: Homo sapiens

<400> SEQUENCE: 13

Glu Leu Thr Gln Ser Pro Val Thr Leu Ser Leu Ser Pro Gly Glu Arg
1               5                   10                  15

Ala Thr Leu Ser Cys Gly Ala Ser Gln Ser Val Ser Ser Asn Leu
            20                  25                  30

-continued

```
Ala Trp Tyr Gln Gln Lys Pro Gly Leu Ala Pro Arg Leu Leu Ile Tyr
        35                  40                  45

Asp Ala Ser Ser Arg Ala Thr Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Ser Ser Leu Ile Thr
                85                  90                  95

Phe Gly Gln Gly Thr Arg Leu Glu Ile Lys
                100                 105
```